United States Patent
Asano et al.

(10) Patent No.: US 11,214,790 B2
(45) Date of Patent: Jan. 4, 2022

(54) HYDROXYNITRILE LYASE

(71) Applicant: Toyama Prefectural University, Toyama (JP)

(72) Inventors: Yasuhisa Asano, Toyama (JP); Takuya Yamaguchi, Toyama (JP)

(73) Assignee: TOYAMA PREFECTURAL UNIVERSITY

(*) Notice: Subject to any disclaimer, the term of this patent is extended or adjusted under 35 U.S.C. 154(b) by 526 days.

(21) Appl. No.: 16/081,476

(22) PCT Filed: Feb. 28, 2017

(86) PCT No.: PCT/JP2017/007910
§ 371 (c)(1),
(2) Date: Nov. 20, 2018

(87) PCT Pub. No.: WO2017/150560
PCT Pub. Date: Sep. 8, 2017

(65) Prior Publication Data
US 2019/0071664 A1    Mar. 7, 2019

(30) Foreign Application Priority Data

Mar. 1, 2016 (JP) .............................. JP2016-038640

(51) Int. Cl.
*C12N 15/52*        (2006.01)
*C12N 9/88*         (2006.01)
(Continued)

(52) U.S. Cl.
CPC ........... *C12N 15/1003* (2013.01); *C12N 9/88* (2013.01); *C12N 15/09* (2013.01); *C12N 15/52* (2013.01);
(Continued)

(58) Field of Classification Search
None
See application file for complete search history.

(56) References Cited

U.S. PATENT DOCUMENTS

| 2009/0170156 A1* | 7/2009 | Asano | ................ C12N 9/88 435/69.1 |
| 2019/0071664 A1* | 3/2019 | Asano | ................ C12N 15/70 |

FOREIGN PATENT DOCUMENTS

| JP | 2000217590 A | 8/2000 |
| JP | 2015167477 A | 9/2015 |

(Continued)

OTHER PUBLICATIONS

Extended European Search Report for corresponding European Application No. 17760025.1; dated Jun. 27, 2019.
(Continued)

*Primary Examiner* — Richard C Ekstrom
(74) *Attorney, Agent, or Firm* — Mendelsohn Dunleavy, P.C.

(57) ABSTRACT

Provided are a method for obtaining an HNL gene and HNL derived from a millipede other than *Chamberlinius hualienensis*, and preparing a practically useable amount of HNL; and a method for producing optically active cyanohydrin using this HNL. A method for producing a millipede-derived HNL gene. A method that includes the selection of a gene having a base sequence that encodes a conserved amino acid sequence TAX1DIX2G (SEQ ID NO: 15) or VPNGDKIH (SEQ ID NO: 16) of millipede-derived HNL from genes present in an organism belonging to the Diplopoda. A protein having an amino acid sequence of any of (1)-(3) and having HNL activity. (1) An amino acid sequence listed in any of SEQ ID NOS: 1, 3, 5, 7, 9, 11, 13, 83, 85, 87, or 89; (2) an amino acid sequence having amino acids deleted, substituted, and/or added in an amino acid sequence of (1); or (3) an amino acid sequence having 90% or greater identity to an amino acid sequence of (1). A method for preparing optically active cyanohydrin by causing this millipede-derived HNL to act on a reaction solvent that contains an aldehyde or the like and a substance that generates hydrogen cyanide or the like.

17 Claims, 14 Drawing Sheets

Specification includes a Sequence Listing.

(51) Int. Cl.
    *C12N 15/09*         (2006.01)
    *C12N 15/10*         (2006.01)
    *C12P 13/00*         (2006.01)
    *C12N 15/70*         (2006.01)
    *C12N 15/85*         (2006.01)
    *C12Q 1/6806*       (2018.01)

(52) U.S. Cl.
    CPC .............. *C12N 15/70* (2013.01); *C12N 15/85* (2013.01); *C12P 13/00* (2013.01); *C12Q 1/6806* (2013.01); *C12Q 2600/16* (2013.01); *C12Y 401/02047* (2013.01)

(56) References Cited

FOREIGN PATENT DOCUMENTS

| WO | WO2006041226 A1 | 4/2006 |
|---|---|---|
| WO | WO2015133462 A1 | 9/2015 |

OTHER PUBLICATIONS

Kuwahara, Yasumasa et al. "Release of Hydrogen Cyanide via a Post-secretion Schotten-Baumann Reaction in Defensive Fluids of Polydesmoid Millipedes." Journal of Chemical Ecology 37.3 (2011): 232-238.

Zagrobelny, Mika et al., "Cyanogenesis in plants and arthropods." Phytochemistry 69.7 (2008): 1457-1468.

Communication pursuant to Article 94(3) EPC for corresponding European application No. 17760025.1; dated Jul. 30, 2020; 5 pages.

Dadashipour, Mohammad, et al. "Discovery and molecular and biocatalytic properties of hydroxynitrile lyase from an invasive millipede, *Chamberlinius hualienensis*." Proceedings of the National Academy of Sciences 112.34 (2015): 10605-10610.

Duffey, S. S., and G. H. N. Towers. "On the biochemical basis of HCN production in the millipede *Harpaphe haydeniana* (Xystodesmidae: Polydesmida)." Canadian Journal of Zoology 56.1 (1978): 7-16.

Lobstein, Julie, et al. "SHuffle, a novel *Escherichia coli* protein expression strain capable of correctly folding disulfide bonded proteins in its cytoplasm." Microbial cell factories 11.1 (2012): 753.

Nuylert, A., et al., "Purification and characterization of hydroxynitrile lyase from millipedes, *Parafontaria laminata*," Biotechnology Reseach Center, Toyama Prefectural University, Asano Active Enzyme Molecule Project, 2016, 3 pages.

Yamaguchi, T. et al., "Molecular cloning of hydroxynitrile lyase from millipedes and heterologous expression in *Eshcerichia coli*," Toyama Pref. University, ERATO, JST, 2016, 3 pages.

International Preliminary Report on Patentability, dated Feb. 20, 2018 for PCT Application No. PCT/JP2017/007910.

Notice of Reasons for Refusal for corresponding Japanese application No. 2018-503346; dated Nov. 24, 2020, 10 pages (Machine Translation).

Bessette, Paul H., et al. "Efficient folding of proteins with multiple disulfide bonds in the *Escherichia coli* cytoplasm." Proceedings of the National Academy of Sciences 96.24 (1999): 13703-13708.

\* cited by examiner

FIG. 3A 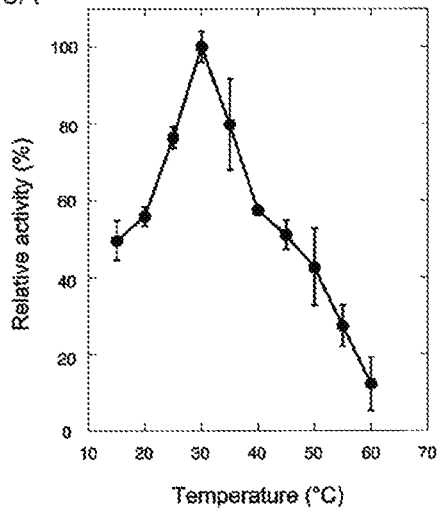

FIG. 3B 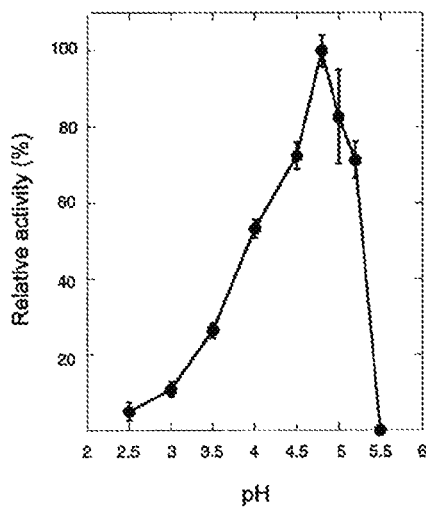

FIG. 4

>NttHNL (SEQ ID:01)
MLFYVSILLVVTLTGAEEEPLTCDKLPKVPVPPLEDFIDSNPLQFAYVLTHTFDCTTRV
YVRPGRLSPTQAATALDIQGSHVIANDFVGGPDNSAILTNCTTGEKTIWHFQYTNLN
TPNGSSYCAYTCNGSAIAEYKCANNNNGTDPLQTQAVEVAKKVPNGDKIHYALDNC
PQHHGCFAFY*

>NttHNL (SEQ ID:02)
ATGCTGTTTTACGTTTCGATTCTTCTAGTGGTCACATTAACTGGAGCTGAGGAGG
AACCATTGACATGCGATAAACTTCCTAAAGTTCCAGTTCCTCCGTTAGAAGATTTT
ATTGATTCGAATCCCTTGCAATTTGCTTACGTTCTGACCCACACTTTCGATTGTAC
CACTAGAGTTTACGTGCGCCCTGGTCGCTTGTCTCCTACCCAGGCTGCAACTGC
ATTGGACATTCAAGGTTCACATGTTATTGCTAATGATTTCGTTGGTGGACCTGATA
ACTCCGCCATACTTACTAATTGTACTACAGGCGAAAAAACTATCTGGCACTTTCAA
TATACTAATTTGAACACCCCAAATGGAAGTTCATATTGCGCTTATACGTGCAATGG
TTCTGCAATTGCAGAGTATAAATGTGCTAATAATAACAATGGAACCGACCCACTCC
AAACTCAAGCAGTTGAAGTTGCTAAGAAAGTTCCAAACGGTGATAAGATTCATTA
TGCCTTGGACAACTGTCCACAACACCATGGTTGTTTTGCTTTCTATTAA

FIG. 5

>NtmHNL(SEQ ID:03)
MLFYVSILLVVALAGAEDEPLTCDKLPKVPVPPLQDFIDSNPLQFAYVLTNTFDCTTR
VYVRPGRLSPTQAATALDIQGSHVIANDFVGGPNNSAILTNCTTGEKTTWYFQYTNL
NTPDGSSYCAYTCNGAAIAEYKCANNNNGTDPLQIQAVEVAKKVPNGDKIHYALAN
CPQHHGCFAFY*

>NtmHNL (SEQ ID:04)
ATGCTGTTTTACGTCTCGATTCTTCTAGTGGTCGCATTAGCTGGAGCTGAGGAC
GAACCATTGACTTGCGATAAACTTCCAAAGTTCCAGTTCCTCCGTTACAAGATT
TTATTGATTCGAATCCCTTGCAATTTGCTTACGTCCTGACCAACACTTTCGATTGT
ACCACTAGAGTTTACGTGCGTCCTGGTCGCTTGTCTCCTACCCAAGCCGCAACT
GCATTGGACATTCAAGGTTCACATGTTATTGCTAATGATTCGTTGGTGGACCTAA
TAACTCCGCCATACTTACTAATTGCACTACAGGCGAAAAACTACCTGGTACTTT
CAATATACTAATCTGAACACCCCAGATGGAAGTTCATATTGCGCTTATACGTGCAA
TGGCGCTGCAATTGCAGAGTATAAATGTGCTAATAATAACAATGGAACCGACCCA
CTCCAAATTCAAGCAGTTGAAGTTGCTAAGAAAGTTCCAAACGGTGATAAGATTC
ATTATGCCTTGGCCAACTGTCCACAACACCATGGCTGTTTTGCTTTCTATTGA

FIG. 6

>OgraHNL(SEQ ID:05)

MLYYVSILLMAVYAVAVADEDPMTCDKLPKVPVPPLEEFIKSNPLQFAYVLTDTFDCTTR
VYVQPARLSPNQAATALDIRGSRIITNDFVGGPNNSAILNNCTTGEKATWYFQYTNLNT
PNGSSYCAYTCNGEEIAEYKCANNNNGTDPLQKQAVEVAKKVPNGDKIHYALDNCPE
HHGCFAFY*

>OgraHNL(SEQ ID:06)

ATGTTGTACTACGTTTCAATACTTTTAATGGCTGTCTATGCTGTGGCTGTAGCGGATG
AAGACCCAATGACTTGCGATAAACTTCCAAAGTTCCAGTTCCTCCTTTAGAGGAAT
TTATTAAGTCAAATCCTTTGCAATTTGCTTACGTTCTGACTGATACCTTTGATTGTACC
ACTCGAGTTTATGTGCAGCCTGCTCGTTTGTCTCCCAACCAAGCGGCAACCGCATT
GGATATTAGAGGTTCCAGAATAATTACTAATGATTTCGTTGGTGGTCCTAATAATTCA
GCTATTCTTAATAACTGTACTACAGGAGAAAAAGCAACTTGGTACTTTCAATACACCA
ATCTGAACACTCCAAATGGAAGCTCCTATTGCGCCTAcACGTGCAATGGAGAAGAAA
TTGCAGAATATAAATGCGCTAATAACAACAACGGAACCGATCCACTTCAAAAACAAG
CGGTAGAAGTTGCTAAAAAGTTCCAAACGGTGATAAGATTCATTATGCCCTGGACA
ACTGTCCTGAACACCATGGCTGTTTTGCTTTCTATTAG

FIG. 7

>PfalHNL(SEQ ID:07)

MTSIIFLTTVALIVMLAELGWAQPSGLTCDQLDKVVPPGISAFISNNPFEFSYVLT
KTFDCTARVYVQPVHGLTNYSGTALDIRGTHIIINDFTIGSDSMTAFLTNCDNGK
KQVWHFQYIDLNDPQGANYCAYSCNGPEIVEYKCTTNTGYISATQRQAVKKA
QLVPNGYKIHLAQDNCPPHPFCPLYY*

>PfalHNL(SEQ ID:08)

ATGACTTCGATCATTTTCCTCACGACTGTAGCACTGATCGTTATGTTGGCCG
AATTGGGCTGGGCTCAACCTTCAGGTCTCACTTGCGACCAACTCGACAAA
GTCGTCCACCTGGCATTAGTGCTTTCATTTCCAACAATCCTTTTGAATTCT
CGTATGTGTTGACTAAAACTTTCGACTGTACCGCACGAGTCTACGTACAGC
CTGTACATGGACTGACCAATTACAGTGGAACTGCACTGGACATCAGAGGAA
CTCACATAATAATTAATGACTTCACCATTGGTTCTGATTCTATGACAGCTTTT
TGACTAATTGCGATAATGGAAAAAACAGGTTTGGCATTTTCAATATATCGAC
CTAAATGATCCCCAAGGTGCCAACTATTGTGCATACTCTTGCAATGGTCCCG
AAATAGTCGAATACAAATGCACTACGAATACTGGATACATATCAGCTACACAA
CGTCAGGCTGTAAAAAAGGCACAATTAGTTCCAAACGGCTATAAGATCCATC
TAGCCCAGGACAATTGCCCTCCTCACCCTTTCTGTCCTCTCTATTACTAA

FIG. 8

>Pton1HNL(SEQ ID:09)

MTSIILLLAAALTVMLAELGWAQPSGLACDQLPKVSPPGISAFISHNPFEFTYVLTDT
FDCTARVYVQPVHGLTNYSGTALDIRGTHIIINDFTIGPDAMTAYLTNCDNDEKQVW
HFQYVDLDDPQGANYCAYFCNGPNIVEYKCTTNTGYISPQQLQAVKEAQSVPNGD
KIHLAQANCPPHPFCPLYY*

>Pton1HNL(SEQ ID:10)

ATGACTTCAATCATTCTCCTCTTGGCTGCAGCACTGACCGTTATGTTGGCCGAAT
GGGCTGGGCTCAACCTTCAGGTCTCGCTTGCGACCAGCTCCCAAAGTCAGC
CCACCAGGCATTAGTGCTTTCATTTCCATAATCCTTTTGAATTCACGTATGTTTT
GACTGACACTTTCGACTGTACCGCACGAGTCTACGTACAGCCTGTACATGGACT
GACCAATTACAGTGGAACTGCACTGGACATCAGAGGAACTCACATCATAATTAAT
GACTTCACCATTGGTCCCGATGCTATGACGGCCTATTTGACTAATTGCGATAATG
ACGAAAACAGGTTTGGCATTTTCAATATGTCGACCTAGATGATCCCCAAGGTG
CCAACTATTGTGCATACTTTTGCAATGGTCCCAACATAGTGGAATACAAATGCACT
ACGAATACTGGATACATATCGCCTCAACAACTCCAGGCTGTAAAAGAGGCACAA
TCAGTCCCAAATGGTGACAAGATCCATCTAGCCCAGGCCAATTGCCCTCCTCAC
CCTTTCTGTCCTCTCTATTACTAA

FIG. 9

>PlamHNL_CDS(SEQ ID:11)

MTSIILLMTVAALIVMLAELGWAQPSPLTCDKLPKVIPPGISAFTSHNPFEFSYVLTND
LDCTARVYVQPVHGLTNYSGTAFDIKGTHITINDFTIGADGLTAYLTNCDTDVKQVWH
FQYVDLGDPQGANYCAYYCEGPEIVEYKCTTNTGYISPRQLQAVKEAQSVPNGDKI
HPAQVNCPPHLYCPLYY*

>PlamHNL(SEQ ID:12)

ATGACTTCGATCATTCTCCTCATGACTGTTGCTGCACTGATCGTTATGTTGGCCG
AATTGGGCTGGGCTCAACCTTCACCTCTCACTTGCGACAAGCTCCCAAAAGTCA
TCCCACCTGGCATTAGTGCTTTCACTTCCCACAATCCTTTTGAATTCTCGTATGT
GTTGACTAACGATCTCGACTGTACCGCACGAGTCTACGTACAGCCTGTACATGG
ACTGACCAATTACAGTGGAACTGCATTTGACATCAAAGGAACTCACATAACAATA
AATGACTTCACCATTGGTGCCGATGGTCTGACAGCCTATTTGACTAATTGTGATA
CTGACGTAAAACAGGTTTGGCATTTTCAATATGTCGACCTAGGTGATCCCCAAGG
TGCCAACTATTGTGCATACTATTGCGAAGGTCCCGAAATAGTGGAATACAAATGC
ACTACGAATACTGGATACATATCGCCTCGACAACTCCAGGCTGTAAAAGAGGCA
CAATCAGTCCCAAATGGTGACAAGATTCATCCAGCCCAGGTCAATTGCCCTCCT
CACCTTTACTGTCCCTCTATTACTAA

FIG. 10

>RspHNL(SEQ ID:13)

MTSIMFSLTLALTAMMAELGWAQPPDGPSCENLPKVCPPGLDAFISHNPFLFEFVL
SDSLDCTTRVYVQPARGYTNYSGTAFDIRKNHIDINDFLIAADCIAYLTNCDTGAKQ
VWYFQYVDLDDPLGANYCAYSCNGASIVEYKCTSNTGYISQKQKDAVAEAKKVPN
GDKIHPGQIGCAYPICPFYS*

>RspNL(SEQ ID:14)

ATGACTTCGATCATGTTCAGCCTGACTTTAGCACTGACTGCTATGATGGCCGAA
TTGGGCTGGGCTCAACCTCCTGACGGCCCTTCCTGCGAAAATCTCCCCAAAGT
CTGCCCACCAGGTCTCGATGCTTTCATTTCCCACAATCCGTTTTTATTCGAGTTT
GTGTTGAGCGACAGTTTGGACTGCACCACGAGTCTACGTGCAGCCTGCAC
GTGGATACACCAATTACAGTGGCACCGCATTTGACATAAGAAAAATCATATAGA
CATTAATGACTTCCTCATCGCTGCTGATTGTATCGCCTATTTGACCAATTGTGATA
CCGGGGCAAAACAGGTTTGGTATTTTCAATATGTCGACCTCGATGATCCCTGG
GTGCCAACTATTGCGCATACTCTTGCAATGGTGCCTCTATAGTGGAATACAAATG
CACTTCCAATACTGGCTATATATCGCAAAGCAAAGGATGCAGTGGCAGAGGC
TAAAAAAGTCCCAAATGGTGACAAGATCCACCCAGGCCAGATCGGCTGCGCTT
ACCCTATCTGCCCCTTCTATAGCTAA

FIG. 13

>PtokHNL(SEQ ID:83)

MetThrSerIleIleLeuLeuThrThrValAlaLeuSerValMetLeuAlaGluLeuGlyTrpAlaValSerAl
aLeuThrCysAspHisLeuProLysValIleProProGlyIleSerAlaPheAlaSerAsnAsnProPheGl
uPheSerTyrValLeuThrAsnAspIleAspCysThrAlaArgValTyrValGlnProValHisGlyLeuThr
AsnTyrSerGlyThrAlaPheAspIleArgGlyThrHisIleThrIleAsnAspPheThrIleAlaProAspGl
yLeuThrAlaTyrLeuThrAsnCysAspThrAspGluLysGlnValTrpAsnPheGlnTyrValAspLeu
AspAspProGlnGlyAlaAsnTyrCysAlaTyrSerCysAsnGlyProGluIleValGluTyrLysCysThr
ThrAsnThrGlyTyrIleSerAlaGlnGlnLeuGlnAlaValLysGluAlaGlnSerValProAsnGlyAspL
ysIleHisLeuAlaGlnValAsnCysProProHisLeuPheCysProLeuTyrTyr

>PtokHNL(SEQ ID:84)

ATGACTTCGATCATTCTCCTCACGACTGTAGCACTGAGCGTTATGTTGGCCGAA
TTGGGCTGGGCTGTGTCAGCATTGACTTGCGACCATCTCCCCAAAGTCATCCC
ACCTGGCATTAGTGCTTTCGCTTCCAACAATCCTTTTGAATTCTCGTATGTGTTG
ACTAACGATATCGATTGTACCGCACGAGTCTATGTACAGCCTGTACATGGACTG
ACCAATTACAGTGGAACTGCATTTGACATCAGAGGAACTCACATAACAATAAATG
ACTTCACCATTGCTCCCGATGGTCTGACAGCCTATTTGACTAATTGTGATACTGA
CGAAAAACAGGTTTGGAATTTTCAATATGTCGACCTAGATGATCCCCAAGGTGC
CAACTATTGTGCATACTCTTGCAATGGTCCCGAAATAGTGGAATACAAATGCACT
ACAAATACTGGATACATATCGGCTCAACAACTCCAAGCTGTAAAAGAGGCACAA
TCAGTCCCGAATGGTGACAAGATCCATCTAGCTCAGGTCAATTGCCCTCCTCAC
CTTTTCTGTCCCTCTATTACTAA

FIG. 14

>Pton2HNL(SEQ ID:85)

MetThrSerIleIleLeuLeuThrThrValAlaLeuIleValMetLeuAlaGluLeuGlyTrpAlaValSerGly
LeuThrCysAspGlnLeuProAsnValIleProProGlyIleSerAlaPheAlaSerAsnAsnProPheGl
uPheSerTyrValLeuThrAsnAspIleAspCysThrAlaArgValTyrValGlnProValHisGlyLeuThr
AsnTyrSerGlyThrAlaPheAspIleArgGlyThrHisIleThrIleAsnAspPheThrIleAlaProAspGl
yLeuThrAlaTyrLeuThrAsnCysAspAsnGlyGluLysGlnValTrpHisPheGlnTyrValAspLeuA
spAspProGlnGlyAlaAsnTyrCysAlaTyrSerCysAsnGlyProGluIleValGluTyrLysCysThrT
hrAsnThrGlyTyrIleSerProGlnGlnLeuGlnAlaValLysGluAlaGlnSerValProAsnGlyAspLy
sIleHisLeuAlaGlnAlaAsnCysProProHisLeuTyrCysProLeuTyrTyr

>Pton2HNL(SEQ ID:86)

ATGACTTCGATCATTCTCCTCACGACTGTAGCACTGATCGTTATGCTGGCCGAA
TTGGGCTGGGCTGTGTCAGGTTTGACTTGCGACCAGCTCCCCAATGTCATCCC
ACCTGGCATTAGCGCTTTCGCTTCCAACAATCCTTTTGAATTCTCGTATGTGTTG
ACTAACGATATCGACTGTACCGCACGAGTCTATGTACAGCCTGTACATGGACTG
ACCAATTACAGTGGAACAGCATTTGACATCAGAGGAACTCACATAACAATAAATG
ACTTCACCATTGCTCCCGATGGTCTGACAGCCTATTTGACTAATTGTGATAATGG
AGAAAAACAGGTTTGGCATTTTCAATATGTCGACCTAGATGATCCCCAAGGTGC
CAACTACTGTGCATACTCTTGCAATGGTCCCGAAATAGTGGAATACAAATGCACT
ACGAATACTGGATACATATCGCCTCAACAACTCCAAGCTGTAAAAGAGGCACAA
TCAGTCCCAAATGGTGACAAGATCCATCTAGCCCAGGCCAATTGCCCTCCTCA
CCTTTACTGTCCTCTCTATTACTAA

FIG. 15

>Pton3HNL(SEQ ID:87)

MetThrSerIleIleLeuLeuThrThrValAlaLeuIleValMetLeuAlaGluLeuGlyTrpAlaGlnProSer
GlyLeuThrCysAspGlnLeuProLysValSerProProGlyIleSerAlaPheThrPheAsnAsnProP
heGluPheSerTyrValLeuThrHisAspIleAspCysThrAlaArgValTyrValGlnProValHisGlyLe
uThrAsnTyrSerGlyThrAlaPheAspIleArgGlyThrHisIleThrIleAsnAspPheThrIleAlaProA
spGlyLeuThrAlaTyrLeuThrAsnCysAspAsnGlyGluLysGlnValTrpHisPheGlnTyrValAsp
LeuAspAspProGlnGlyAlaAsnTyrCysAlaTyrSerCysAsnGlySerGluIleValGluTyrLysCys
ThrThrAsnThrGlyTyrIleSerProGlnGlnLeuGlnAlaValLysGluAlaGlnSerValProAsnGlyA
spLysIleHisProAlaGlnAlaAsnCysProProHisLeuTyrCysProLeuTyrTyr

>Pton3HNL(SEQ ID:88)

ATGACTTCGATCATTCTCCTCACGACTGTAGCACTGATCGTTATGTTGGCCGAAT
TGGGCTGGGCTCAACCTTCAGGTCTCACTTGCGACCAGCTCCCCAAAGTCAG
TCCACCTGGCATTAGTGCTTTCACTTTCAACAATCCTTTTGAATTCTCGTATGTG
CTGACTCACGATATCGACTGTACCGCACGAGTCTACGTACAGCCTGTACATGGA
CTGACCAATTACAGTGGAACTGCATTTGACATCAGAGGAACTCACATAACAATA
AATGACTTCACCATTGCTCCCGATGGTCTGACAGCCTATTTGACTAATTGTGATA
ATGGAGAAAAACAGGTTTGGCATTTTCAATATGTCGACCTAGATGATCCCCAAG
GTGCCAACTATTGTGCATACTCTTGCAATGGTTCCGAAATAGTGGAATACAAATG
CACTACGAATACTGGATACATATCGCCTCAACAACTCCAGGCTGTAAAAGAGGC
ACAATCAGTCCCAAATGGTGACAAGATCCATCCAGCCCAGGCCAATTGCCCTC
CTCACCTTTACTGTCCTCTCTATTACTAA

FIG. 16

>RssHNL(SEQ ID:89)

MetThrSerIleMetLeuCysLeuThrLeuAlaLeuThrAlaMetMetAlaGluLeuGlyCysAlaGlnPr
oAlaGluGlyProSerCysGluAsnLeuProLysValValProProGlyIleAspAlaPheValSerHisAs
nProPheGluPheGluPheValLeuSerAsnSerLeuAspCysThrAlaArgValTyrValGlnProAla
ArgGlyTyrThrAsnTyrSerGlyThrAlaPheAspIleArgLysAsnHisIleAspIleAsnAspPheLeuIl
eGlyAlaAspGlyLeuThrAlaTyrLeuThrAsnCysAspThrGlyAlaLysGlnValTrpHisPheGlnT
yrThrAspLeuAspAspProLeuGlyAlaAsnTyrCysAlaTyrSerCysAspGlyAlaSerIleValGluT
yrLysCysThrSerAsnThrGlyTyrIleSerGlnLysGlnLysAspAlaValAlaGluAlaLysLysValPro
AsnGlyAspLysIleHisProGlyGlnValAsnCysProProAsnProPheCysProPheTyrSer

>RssHNL(SEQ ID:90)

ATGACTTCGATCATGCTCTGTTTAACTTTAGCACTGACTGCTATGATGGCCGAAT
TGGGCTGTGCTCAACCTGCTGAAGGCCCTTCCTGCGAAAATCTCCCCAAAGTC
GTCCCACCAGGCATCGATGCTTTCGTTTCCCACAATCCTTTTGAATTTGAGTTT
GTGTTGAGCAACAGTTTGGACTGCACCGCACGTGTCTACGTGCAGCCTGCAC
GTGGATACACCAATTACAGTGGCACCGCATTTGATATAAGAAAAAATCATATTGA
CATTAACGACTTTCTGATCGGTGCTGATGGATTGACCGCCTATTTAACCAATTGT
GATACCGGGGCAAAACAAGTTTGGCATTTTCAATATACCGACCTCGATGATCCC
CTGGGTGCCAACTATTGTGCATACTCATGCGATGGTGCCTCTATAGTGGAATAC
AAATGCACTTCCAATACTGGCTACATATCGCAAAAGCAAAAGGATGCAGTGGCA
GAGGCTAAAAAAGTCCCAAATGGTGACAAGATCCACCCAGGCCAGGTCAATTG
CCCTCCTAACCCTtTCTGCCCCTTCTATAgctaa

HYDROXYNITRILE LYASE

TECHNICAL FIELD

The present invention relates to a method for cloning millipede-derived hydroxynitrile lyase (HNL) genes, enzymes produced by expression of these genes, and a method for manufacturing an optically active cyanohydrin using an expressed enzyme.

CROSS-REFERENCE TO RELATED APPLICATIONS

The priority claim for this application is based on Japanese Patent Application No. 2016-038640 filed on Mar. 1, 2016, the entire disclosure whereof is hereby specifically incorporated by reference.

BACKGROUND ART

Optically active cyanohydrins are important intermediates in the manufacture of drugs and fine chemicals. A method of reacting an aldehyde or ketone and a cyanide donor with a hydroxynitrile lyase has been proposed as a cyanohydrin manufacturing method (PTL 1). An (R)-hydroxynitrile lyase discovered in *Chamberlinius hualienensis* has higher specific activity and greater stability with respect to heat and pH than hydroxynitrile lyase discovered in plants (PTL 2 and NPL 2).

CITATION LIST

Patent Literature

[PTL 1] Japanese Patent Application Publication No. 2000-217590
[PTL 2] Japanese Patent Application Publication No. 2015-167477

Non Patent Literature

[NPL 1] Dadashipur et al., Proc. Natl. Acad. Sci. USA. 112, 10605-10610 (2015)

SUMMARY OF INVENTION

Technical Problem

In PTL 2, the (R)-hydroxynitrile lyase discovered in *Chamberlinius hualienensis* is expressed in yeast, but the level of expression is very low, and no *E. coli* expression system has been constructed, making large-volume preparation difficult.

Although it is inferred that other millipedes may have hydroxynitrile lyase (HNL), the enzymes and enzyme genes have not been discovered, and no cloning methods have been established for other millipede-derived HNL genes.

It is therefore an object of the present invention to obtain (provide) an HNL gene and HNL derived from a millipede other than *Chamberlinius hualienensis*, to establish an expression system for the resulting HNL, and to provide a method for preparing a practically useful amount of HNL. It is another object of the present invention to provide a method for manufacturing an optically active cyanohydrin using the provided HNL.

Solution to Problem

The inventors conducted extensive research in order to solve these problems.

The inventors discovered that HNL genes from various millipedes could be cloned using degenerate primers having specific sequences out of the sequences that are conserved among millipede HNL genes, and we obtained HNL genes and HNL from various millipedes by this method. We also discovered that HNL could be manufactured by using cultured insect cells and specific *E. coli* to express newly-discovered HNL genes. Furthermore, we discovered that an optically active cyanohydrin could be manufactured using the expressed HNL, thereby perfecting the present invention.

The present invention is as follows.

[1]

A method for manufacturing a millipede-derived hydroxynitrile lyase (hereunder, HNL) gene, comprising:
selecting a gene having at least one of a nucleotide sequence encoding for a conserved amino acid sequence $TAX^1DIX^2G$ (SEQ ID NO:15) (wherein $X^1$ is L or F, and $X^2$ is R or K) and a nucleotide sequence encoding for a conserved amino acid sequence VPNGDKIH (SEQ ID NO:16) of millipede-derived HNL from the genes present in an organism belonging to the Diplopoda.

[2]

The method according to [1], wherein selection of the gene is accomplished by performing PCR using a gene present in an organism belonging to the Diplopoda as a template, and using at least one DNA comprising a nucleotide sequence encoding for the conserved amino acid sequence as a primer.

[3]

The method according to [1], wherein selection of the gene is accomplished by performing DNA-DNA hybridization using a gene present in an organism belonging to the Diplopoda as a template, and using DNA comprising a nucleotide sequence encoding for the conserved amino acid sequence as a probe.

[4]

The method according to [1], wherein selection of the gene is accomplished by sequencing genes present in an organism belonging to the Diplopoda, and selecting a gene having a nucleotide sequence encoding for the conserved amino acid sequence from the sequenced gene sequences.

[5]

A method according to any one of [1] to [4], wherein the gene present in an organism belonging to the Diplopoda is genome DNA extracted from an organism belonging to the Diplopoda, or cDNA obtained by reverse transcription of RNA extracted from an organism belonging to the Diplopoda.

[6]

The method according to [2], wherein the primers are the degenerate primers HNL-FW and HNL-RV or HNL-FW2 and HNL-RV2 below.

```
HNL-FW:
                            (SEQ ID NO: 21)
CTGCAACTGCATTGGAMATTCAAGG

HNL-RV:
                            (SEQ ID NO: 22)
ATGAATCTTRTCRCCGTTTGGAAC

HNL-FW2:
                            (SEQ ID NO: 23)
SSAACTGCATTGGAYATMMRAGG

HNL-RV2:
                            (SEQ ID NO: 24)
ATGAATCTTRTCRCCRTTTGGRAC
```

[7]

A method according to any one of [1] to [6], wherein the organism belonging to the Diplopoda is *Nedyopus tambanus* mangaesinus, Oxidus gracilis, Parafontaria falcifera, Parafontaria laminata, Parafontaria tonominea or Riukiaria sp.

[8]

A method for manufacturing millipede-derived HNL, comprising:

preparing a millipede-derived HNL gene by a method according to any one of [1] to [7], and causing the resulting HNL gene to be expressed in host cells to obtain the HNL.

[9]

The method according to [8], wherein the host cells are cultured insect cells.

[10]

The method according to [8], wherein the host cells are E. coli cells having disulfide bond isomerase expressing ability.

[11]

A gene having any of the nucleotide sequence of (4) to (6) below:

(4) a nucleotide sequence having a nucleotide sequence of any of SEQ ID NOS:2, 4, 6, 8, 10, 12, 14, 84, 86, 88 or 90 of the sequence listing, and encoding for a protein having HNL activity;

(5) a nucleotide sequence having a nucleotide sequence of any of SEQ ID NOS:2, 4, 6, 8, 10, 12, 14, 84, 86, 88 or 90 of the sequence listing with 1 to 50 nucleotide deletions, substitutions and/or additions therein, and encoding for a protein having HNL activity; or (6) a nucleotide sequence having a nucleotide sequence that hybridizes under stringent conditions with a nucleotide sequence of any of SEQ ID NOS:2, 4, 6, 8, 10, 12, 14, 84, 86, 88 or 90 of the sequence listing, and encoding for a protein having HNL activity.

[12]

A plasmid comprising the gene of [11] contained in a vector.

[13]

A transformant comprising a host containing a plasmid comprising the gene of [11] contained in a vector in such a way that the gene can be expressed, wherein the host is an insect cell or an E. coli having disulfide bond isomerase expressing ability.

[14]

A method for manufacturing a millipede-derived HNL, comprising culturing the transformant according to [13] and separating the HNL from the culture.

[15]

The method according to [14], wherein the host is cultured insect cells, and the HNL gene is an HNL gene derived from Nedyopus tambanus mangaesinus, Oxidus gracilis, Parafontaria falcifera, Parafontaria laminata, Parafontaria tonominea or Riukiaria sp.

[16]

The method according to [14], wherein the host is an E. coli having disulfide bond isomerase expressing ability, and the HNL gene is an HNL gene derived from Nedyopus tambanus mangaesinus, Oxidus gracilis or Parafontaria laminata.

[17]

A protein having an amino acid sequence of any of (1) to (3) below, and having HNL activity:

(1) An amino acid sequence of any of SEQ ID NOS:1, 3, 5, 7, 9, 11, 13, 83, 85, 87 or 89 of the sequence listing;

(2) An amino acid sequence of any of SEQ ID NOS:1, 3, 5, 7, 9, 11, 13, 83, 85, 87 or 89 of the sequence listing with 1 to 50 amino acids deletions, substitutions and/or additions therein; or (3) An amino acid sequence having at least 90% identity with an amino acid sequence of any of SEQ ID NOS:1, 3, 5, 7, 9, 11, 13, 83, 85, 87 or 89 of the sequence listing.

[18]

The protein according to [17], having any of the amino acid sequences of (1) to (3) below, and having HNL activity:

(1) an amino acid sequence of SEQ ID NO:85 or 87 of the sequence listing;

(2) an amino acid sequence of SEQ ID NO:85 or 87 of the sequence listing with 1 to 50 amino acid deletions, substitutions and/or additions therein; or (3) an amino acid sequence having at least 90% identity with an amino acid sequence of SEQ ID NO:85 or 87 of the sequence listing.

[19]

A method for manufacturing an optically active cyanohydrin, comprising reacting a millipede-derived HNL with a reaction solution containing an aldehyde or ketone and hydrogen cyanide or a substance that produces cyanide ions in the reaction system to produce an optically active cyanohydrin, wherein the millipede-derived HNL is a protein according to [17] or [18] or a transformant according to [13].

Advantageous Effects of Invention

With the present invention, HNL genes can be cloned from various millipede species. Millipede-derived (R)-HNL having strong specific activity and heat stability can also be easily prepared with cultured insect cells and specific recombinant E. coli, and used to manufacture an optically active cyanohydrin. Because optically active cyanohydrins are important intermediates in the manufacture of drugs and fine chemicals, the present invention is of greater industrial utility.

BRIEF DESCRIPTION OF DRAWINGS

FIG. 2A shows optimum temperature, FIG. 2B optimum pH, FIG. 2C heat stability, and FIG. 2D pH stability.

FIGS. 3A-3B show the effects of heat and pH on NtmHNL purified from *E. coli*. FIG. 3A shows optimum temperature, and FIG. 3B shows optimum pH.

FIG. 4 shows the amino acid sequence of the NttHNL protein (SEQ ID NO:1) and the nucleotide sequence of the NttHNL gene (SEQ ID NO:2).

FIG. 5 shows the amino acid sequence of the NtmHNL protein (SEQ ID NO:3), and the nucleotide sequence of the NtmHNL gene (SEQ ID NO:4).

FIG. 6 shows the amino acid sequence of the OgraHNL protein (SEQ ID NO:5), and the nucleotide sequence of the OgraHNL gene (SEQ ID NO:6).

FIG. 7 shows the amino acid sequence of the PfalHNL protein (SEQ ID NO:7), and the nucleotide sequence of the PfalHNL gene (SEQ ID NO:8).

FIG. 8 shows the amino acid sequence of the Pton1HNL protein (SEQ ID NO:9), and the nucleotide sequence of the Pton1HNL gene (SEQ ID NO:10).

FIG. 9 shows the amino acid sequence of the PlamHNL protein (SEQ ID NO:11), and the nucleotide sequence of the PlamHNL gene (SEQ ID NO:12).

FIG. 10 shows the amino acid sequence of the RspHNL protein (SEQ ID NO:13), and the nucleotide sequence of the RspHNL gene (SEQ ID NO:14).

FIG. 13 shows the amino acid sequence of the PtokHNL protein (SEQ ID NO:83) and the nucleotide sequence of the PtokHNL gene (SEQ ID NO:84).

FIG. 14 shows the amino acid sequence of the Pton2HNL protein (SEQ ID NO:85) and the nucleotide sequence of the Pton2HNL gene (SEQ ID NO:86).

FIG. 15 shows the amino acid sequence of the Pton3HNL protein (SEQ ID NO:87) and the nucleotide sequence of the Pton3HNL gene (SEQ ID NO:88).

FIG. 16 shows the amino acid sequence of the RssHNL protein (SEQ ID NO:89) and the nucleotide sequence of the RssHNL gene (SEQ ID NO:90).

DESCRIPTION OF EMBODIMENTS

Method for Manufacturing HNL Gene

Figure 1:
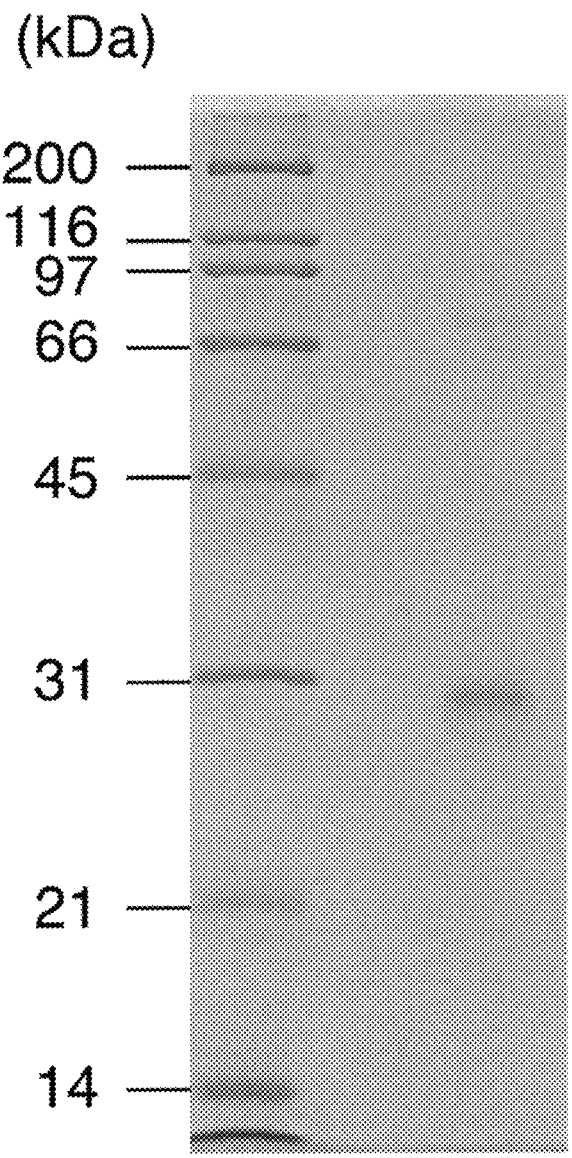
FIG. 1 shows the results of an SDS-PAGE analysis of NttHNL purified from *Nedyopus tambanus tambanus*. Lane 1 shows the Broad Range Marker (Bio-Rad), and Lane 2 shows purified HNL from *Nedyopus tambanus tambanus* (NttHNL).

The present invention relates to a method for manufacture a millipede-derived hydroxynitrile lyase (HNL) gene.

This method comprises the selection of a gene having at least one of a nucleotide sequence encoding for a conserved amino acid sequence TAX$^1$DIX$^2$G (SEQ ID NO:15) (wherein X$^1$ is L or F, and X$^2$ is R or K) and a nucleotide sequence encoding for a conserved amino acid sequence VPNGDKIH (SEQ ID NO:16) of millipede-derived HNL from the genes present in an organism belonging to the Diplopoda.

No methods have been established for cloning HNL genes from millipedes other than *Chamberlinius hualienensis*. Therefore, the inventors searched for sequences that are conserved among millipede-derived HNL genes, and discovered that the amino acid sequences of SEQ ID NOS:15 and 16 are conserved amino acid sequences of millipede-derived HNL.

The conserved amino acid sequence of millipede HNL of SEQ ID NO:15 is TAX$^1$DIX$^2$G, in which X$^1$ is L or F and X$^2$ is R or K. There are four combinations of X$^1$ and X$^2$, which specifically are as follows.

```
                                (SEQ ID NO: 17)
        TALDIRG (SEQ ID NO: 18)
        TALDIKG (SEQ ID NO: 19)
        TAFDIRG (SEQ ID NO: 20)
        TAFDIKG
```

The conserved amino acid sequence of millipede-derived HNL of SEQ ID NO:16 is VPNGDKIH.

The nucleotide sequences encoding for these conserved amino acid sequences are not particularly limited, but examples include the degenerate primers HNL-FW (SEQ ID NO:21) and HNL-RV (SEQ ID NO:22), and the degenerate primers HNL-FW2 (SEQ ID NO:23) and HNL-RV (SEQ ID NO:24).

Furthermore, as shown in the examples, it is now possible for the first time to clone HNL genes from various millipedes by using primers (degenerate primers) having nucleotide sequences encoding for conserved amino acid sequences.

The examples show the cloning of HNL genes from various millipedes using degenerate primers as discussed above, but the present invention encompasses all methods comprising the selection of genes having at least one of the nucleotide sequences encoding for conserved amino acid sequences of millipede-derived HNL. Examples of such methods include the methods of (1) to (3) below.

(1) A method in which selection of the gene is accomplished by performing PCR using a gene present in an organism belonging to the Diplopoda as a template, and using at least one DNA comprising a nucleotide sequence encoding for the conserved amino acid sequence as a primer.

(2) A method in which selection of the gene is accomplished by performing DNA-DNA hybridization using a gene present in an organism belonging to the Diplopoda as a template, and using DNA comprising a nucleotide sequence encoding for the conserved amino acid sequence as a probe.

(3) A method in which selection of the gene is accomplished by sequencing genes present in an organism belonging to the Diplopoda, and selecting a gene having a nucleotide sequence encoding for the conserved amino acid sequence from the sequenced gene sequences.

The gene present in an organism belonging to the Diplopoda used in the method of the present invention may be genome DNA extracted from an organism belonging to the Diplopoda, or cDNA obtained by reverse transcription of RNA extracted from an organism belonging to the Diplopoda for example. Known methods may be used appropriately as the method for extracting the genome DNA and the method for preparing the cDNA by reverse transcription from the RNA.

Method (1):

The gene present in an organism belonging to the Diplopoda that is used as a template may be genome DNA extracted as described above or cDNA, and is preferably cDNA, and PCR is performed using such DNA as a template and at least one DNA comprising a nucleotide sequence encoding for the conserved amino acid sequences of SEQ ID NOS:15 and 16 above as a primer. The nucleotide sequences of the primer are not particularly limited as long as it encodes for a conserved amino acid sequence of SEQ ID NOS:15 and 16, but examples include the following degenerate primer sets HNL-FW and HNL-RV, and HNL-FW2 and HNL-RV2. The HNL gene from the organism can be amplified by PCR using these degenerate primers.

```
HNL-FW:
                                (SEQ ID NO: 21)
CTGCAACTGCATTGGAMATTCAAGG

HNL-RV:
                                (SEQ ID NO: 22)
ATGAATCTTRTCRCCGTTTGGAAC

HNL-FW2:
                                (SEQ ID NO: 23)
SSAACTGCATTGGAYATMMRAGG
```

HNL-RV2:

(SEQ ID NO: 24)

ATGAATCTTRTCRCCRTTTGGRAC

Method (2):

The gene present in an organism belonging to the Diplopoda that is used as a template may genome DNA extracted as described above or cDNA, and is preferably extracted genome DNA, and DNA-DNA hybridization is performed with such DNA as a template and at least one DNA comprising a nucleotide sequence encoding for the conserved amino acid sequences of SEQ ID NOS:15 and 16 above as a probe. A known method may be used appropriately for DNA-DNA hybridization. The nucleotide sequence of the probe is not particularly limited as long as it encodes for a conserved amino acid sequence of SEQ ID NOS:15 or 16 above, and for example it may be a nucleotide sequence comprising nucleotide sequences similar to the degenerate primers HNL-FW and HNL-RV above, or parts of these nucleotide sequences. DNA-DNA hybridization is performed using these probes to obtain the HNL gene from the organism. The HNL gene obtained by DNA-DNA hybridization can then be amplified appropriately by a known amplification method such as PCR.

Method (3):

A gene present in an organism belonging to the Diplopoda is sequenced. The target of sequencing is genome DNA extracted as described above or cDNA. Known methods may be used appropriately as the sequencing methods. A gene having a nucleotide sequence encoding for the conserved amino acid sequence is then selected from the sequenced gene sequences.

The organism belonging to the Diplopoda is not particularly limited. Examples of organisms belonging to the Diplopoda include *Epanerchodus* species in the Polydesmidae family of the Polydesmida, *Ampelodesmus* species in the Pyrgodesmidae family of the Polydesmida, and *Corypholophus* species in the Opisotretidae family of the Polydesmida.

The examples show that HNL genes could be cloned from *Nedyopus tambanus mangaesinus* and *Oxidus gracilis* in the Paradoxosomatidae family of the Polydesmida, from *Parafontaria falcifera, Parafontaria laminata* and *Parafontaria tonominea* in the Xystodesmidae family of the Polydesmida, and from *Riukiaria* species.

The cDNA preparation methods and PCR methods using cDNA templates are known methods. These can be implemented with reference to the examples using HNL-FW and HNL-RV above as the degenerate primers.

HNL Gene

The present invention relates to a gene having any of the nucleotide sequences of (4) to (6) below:

(4) a nucleotide sequence having a nucleotide sequence of any of SEQ ID NOS:2, 4, 6, 8, 10, 12, 14, 84, 86, 88 and 90 of the sequence listing, and encoding for a protein having HNL activity;

(5) a nucleotide sequence having a nucleotide sequence of any of SEQ ID NOS:2, 4, 6, 8, 10, 12, 14, 84, 86, 88 and 90 of the sequence listing with 1 to 50 nucleotide deletions, substitutions and/or additions therein, and encoding for a protein having HNL activity; or (6) a nucleotide sequence having a nucleotide sequence that hybridizes under stringent conditions with a nucleotide sequence of any of SEQ ID NOS:2, 4, 6, 8, 10, 12, 14, 84, 86, 88 and 90 of the sequence listing, and encoding for a protein having HNL activity.

Genes of (4) having the nucleotide sequences of SEQ ID NOS:2, 4, 6, 8, 10, 12, 14, 84, 86, 88 and 90 of the sequence listing are HNL genes from *Nedyopus tambanus tambanus, Nedyopus tambanus mangaesinus, Oxidus gracilis, Parafontaria falcifera, Parafontaria tonominea, Parafontaria laminata*, one species of *Riukiaria, Parafontaria tokaiensis, Parafontaria tonominea, Parafontaria tonominea* and a *Riukiaria* species, respectively.

Methods for measuring the HNL activity of the "proteins having HNL activity" described in (4), (5) and (6) are described under "Methods for measuring (R)-mandelonitrile synthesis activity" in the examples.

The range of the "1 to 50" in the "nucleotide sequence with 1 to 50 nucleotide deletions, substitutions and/or additions therein" as described in the Description is not particularly limited, but may for example be 1 to 40, or preferably 1 to 30, or more preferably 1 to 20, or still more preferably 1 to 10, or yet more preferably 1 to 5, or especially about 1 to 3.

A gene having a nucleotide sequence of any of SEQ ID NOS:2, 4, 6, 8, 10, 12, 14, 84, 86, 88 and 90 of the sequence listing with one or more nucleotide deletions, substitutions and/or additions therein, and encoding for a protein having HNL activity (these genes are generally called mutant genes below), can be prepared by any method known to those skilled in the art, such as chemical synthesis, genetic engineering techniques or mutagenesis, based on data about the nucleotide sequence of SEQ ID NOS:2, 4, 6, 8, 10, 12, 14, 84, 86, 88 or 90.

For example, it can be prepared by a method of bringing DNA having the nucleotide sequence of SEQ ID NO:2, 4, 6, 8, 10, 12, 14, 84, 86, 88 or 90 of the sequence listing into contact with an agent that acts as a mutagen, or by a method of exposure to UV rays, or by genetic engineering techniques or the like. Site-specific mutagenesis, which is one of the genetic engineering technique, is useful because it can introduce specific mutations into specific sites, and this technique can be implemented by the methods described in Molecular Cloning 2nd Edition, Current Protocols in Molecular Biology or the like.

The aforementioned nucleotide sequence that "hybridizes under stringent conditions" means a nucleotide sequence of DNA obtained by colony hybridization, plaque hybridization, Southern blot hybridization or the like using DNA as a probe, and for example may be DNA or the like that has been identified using DNA from a colony or plaque or a fragment of such DNA immobilized on a filter, by performing hybridization at 65° C. with 0.7 to 1.0 M of NaCl, and then washing the filter at 65° C. using 0.1 to 2×SSC solution (1×SSC solution=150 mM sodium chloride, 15 mM sodium citrate). Hybridization may be performed by the methods described in Molecular Cloning, 2nd Edition or the like.

DNA that hybridizes under stringent conditions may be DNA having at least a certain degree of identity with the nucleotide sequence of the DNA used as a probe, and may for example be DNA having at least 90%, or preferably at least 93%, or more preferably at least 95%, or still more preferably at least 98%, or still more preferably at least 99% identity.

The method for obtaining the gene of the present invention is not particularly limited, but preferably it is obtained by the HNL gene manufacturing method of the present invention.

The present invention encompasses a plasmid comprising the gene of the present invention contained in a vector. The present invention also encompasses a transformant comprising the plasmid of the present invention in a host organism in such a way that a HNL encoded for by the gene of the present invention can be expressed. Examples of the host organism included cultured insect cells, and *E. coli* having disulfide bond isomerase expressing ability.

The type of vector used in the present invention is not particularly limited, and may for example be an independently replicating vector (such as a plasmid), or one that is incorporated into the genome of a host cell when introduced into a host cell, and is then replicated together with the host chromosome. Preferably, the vector is an expression vector. In an expression vector, the gene is bound functionally to elements necessary for transcription (such as a promoter and the like). A promoter is a DNA sequence exhibiting transcription activity in a host cell, and is selected appropriately according to the type of host. That is, the vector used for the plasmid of the present invention is not particularly limited as long as it can express the HNL gene of the present invention in a host cell. Examples of such expression vectors include pFastbac1, BacPAK6, pIEx-1 and pBiEx-1 in the case of cultured insect cells.

Examples of insect cell-operable promoters include the polyhedrin promoter, P10 promoter, basic protein promoter of *Autographa californica* nuclear polyhedrosis virus, Baculovirus immediate early gene 1 promoter and Baculovirus 39k delayed early gene promoter.

In the case of *E. coli*, examples of expression vectors include pUC19 (Takara Bio Inc.), pBluescript, pET28, pCDF, pRSF and the like. Examples of *E. coli*-operable promoters include the lac, trp or tac promoter.

Method for Manufacturing Millipede-Derived HNL

The present invention encompasses methods for manufacturing millipede-derived HNL.

The method (1) for manufacturing a millipede-derived HNL comprises preparing a millipede-derived HNL gene by the method of the present invention, and expressing the resulting HNL gene using a cultured insect cell as the host to obtain HNL.

In the method (2) for manufacturing a millipede-derived HNL comprises preparing a millipede-derived HNL gene by the method of the present invention, and expressing the resulting HNL gene using an *E. coli* as the host to obtain HNL, with the *E. coli* being an *E. coli* having disulfide bond isomerase expressing ability.

The method (3) for manufacturing a millipede-derived HNL is an HNL manufacturing method that comprises culturing the transformant of the present invention and isolating HNL from the culture.

Specific examples of the method (3) include a method (3-1) in which the host is a cultured insect cell and the HNL gene is an HNL gene from *Nedyopus tambanus mangaesinus, Oxidus gracilis, Parafontaria falcifera, Parafontaria laminata, Parafontaria tonominea* or *Riukiaria* sp., and a method (3-2) in which the host is an *E. coli* having disulfide bond isomerase expressing ability, and the HNL gene is an HNL gene from *Nedyopus tambanus mangaesinus, Oxidus gracilis* or *Parafontaria laminata.*

In the method (3-1) for manufacturing a millipede-derived HNL, the HNL is obtained by expressing an HNL gene from *Nedyopus tambanus mangaesinus, Oxidus gracilis, Parafontaria falcifera, Parafontaria laminata, Parafontaria tonominea* or *Riukiaria* sp. using an insect cell as the host.

In the method (3-2) for manufacturing a millipede-derived HNL, the HNL is obtained by expressing an HNL gene from *Nedyopus tambanus mangaesinus, Oxidus gracilis* or *Parafontaria laminata* using an *E. coli* as the host, with the *E. coli* being an *E. coli* having disulfide bond isomerase expressing ability.

In the case of the methods (1) and (3-1) using insect cells as the host, a recombinant gene transfer vector and Baculovirus can be co-introduced into insect cells by known methods to obtain a recombinant virus in the insect cell culture supernatant, after which insect cells can be infected with the recombinant virus and made to express the protein. *Autographa californica* nuclear polyhedrosis virus, a virus that infects insects of the family Coleoptera, can be used for example as the Baculovirus.

Sf9 or Sf21 *Spodoptera frugiperda* ovarian cells (Baculovirus Expression Vectors, a Laboratory Manual, W. H. Freeman and Company, New York, 1992) or HiFive *Trichoplusia ni* ovarian cells (Invitrogen) or the like may be used as the insect cells. The method for co-introducing the recombinant gene introduction vector and this Baculovirus into insect cells to prepare the recombinant virus may be the calcium phosphate method or lipofection method for example.

In the case of the methods (2) and (3-2) using *E. coli* host cells, an *E. coli* having disulfide bond isomerase expression ability or an *E. coli* having thioredoxin reductase and glutathione reductase mutations is used. An example of an *E. coli* having disulfide bond isomerase expression ability is SHuffle T7. Examples of *E. coli* having mutations in thioredoxin reductase and glutathione reductase include the Origami and Rosetta-gami *E. coli* strains (Merck Millipore). The *E. coli* can be transformed for example by the protoplast method or using competent cells by a known method.

The resulting transformant is cultured in suitable nutrient medium under conditions that allow expression of the introduced gene. The HNL can be isolated and purified from the transformant culture by common protein isolation and purification methods. For example, when the HNL is expressed in a dissolved state in the cells, the cells can be collected by centrifugation after completion of culture, suspended in an aqueous buffer solution, and crushed with an ultrasonic crusher or the like, and a cell-free extract obtained. This cell-free extract can then be centrifuged, and the HNL can be obtained as a purified preparation from the resulting supernatant by an common protein separation and purification method, or in other words by a method or combination of methods such as solvent extraction, salting out with ammonium sulfate or the like, desalting, precipitation with an organic solvent, anion exchange chromatography using a resin such as diethylaminoethyl (DEAE) sepharose, cation exchange chromatograph using a resin such as S-Sepharose FF (Pharmacia Co.), hydrophobic chromatography using a resin such as butyl sepharose or phenyl sepharose, gel filtration using a molecular sieve, affinity chromatography, chromatographic focusing, and electrophoretic methods such as isoelectric focusing electrophoresis.

Protein Having HNL Activity

The present invention relates to a protein having any of the amino acid sequences of (1) to (3) below, and having HNL activity:

(1) an amino acid sequence of SEQ ID NOS:1, 3, 5, 7, 9, 11, 13, 83, 85, 87 or 89 of the sequence listing;

(2) an amino acid sequence of SEQ ID NOS:1, 3, 5, 7, 9, 11, 13, 83, 85, 87 or 89 of the sequence listing with 1 to 50 amino acid deletions, substitutions and/or additions therein; or (3) an amino acid sequence having at least 90% identity with an amino acid sequence of any of SEQ ID NOS:1, 3, 5, 7, 9, 11, 13, 83, 85, 87 or 89 of the sequence listing.

Proteins (1) having the amino acid sequences of SEQ ID NOS:1, 3, 5, 7, 9, 11, 13, 83, 85, 87 and 89 of the sequence listing are HNLs from *Nedyopus tambanus tambanus, Nedyopus tambanus mangaesinus, Oxidus gracilis, Parafontaria falcifera, Parafontaria tonominea, Parafontaria laminata*, one species of *Riukiaria, Parafontaria tokaiensis, Parafontaria tonominea, Parafontaria tonominea* and a *Riukiaria* species, respectively. The proteins having the amino acid sequences of SEQ ID NOS:9, 85 and 87 are all HNLs from *Parafontaria tonominea*, but collected from different locations.

Methods for measuring the HNL activity of the protein having HNL activity of the present invention are described under "Methods for measuring (R)-mandelonitrile synthesis activity" in the examples.

The protein (2) of the present invention is a protein comprising the amino acid sequence of SEQ ID NOS:1 of the sequence listing with 1 to 50 amino acids deletions, substitutions and/or additions therein. The range of the "1 to 50" in the "amino acid sequence with 1 to 50 amino acid deletions, substitutions and/or additions therein" means that a protein having a deletion or the like is an enzyme having HNL activity. From the standpoint of maximizing the percentage of proteins having the HNL activity, the range of "1 to 50" may be 1 to 40, or preferably 1 to 30, or more preferably 1 to 20, or still more preferably 1 to 10, or yet more preferably 1 to 7, or most preferably 1 to 5, or especially about 1 to 3.

The protein (3) of the present invention is a protein having an amino acid sequence having at least 90% identity with the amino acid sequence of SEQ ID NO:1 of the sequence listing. Identity as defined in "an amino acid having at least 90% identity with the amino acid sequence of SEQ ID NO:2 of the sequence listing" is not particularly limited as long as the protein having this amino acid sequence identity is an enzyme having the HNL activity. This amino acid sequence identity is not particularly limited as long as it is at least 90%, but is preferably at least 95%, or more preferably at least 96%, or still more preferably at least 97%, or yet more preferably at least 98%, or especially at least 99%.

The method for obtaining the protein having HNL activity of the present invention is not particularly limited, and it may be a chemically synthesized protein, or a recombinant protein prepared by genetic engineering techniques. The protein having HNL activity of the present invention can be prepared by a manufacturing method wherein a gene encoding for the protein having HNL activity is loaded onto a vector, and a host cell is transformed with this vector, after which the transformed host cell is cultured so that the protein encoded for by the gene accumulates in the culture, and the accumulated protein is collected. The method of the present invention described above is an example of one method for obtaining a gene encoding for the protein having HNL activity. The protein preparation method of the present invention may for example be the method described above for manufacturing the millipede-derived HNL of the present invention.

Method for Manufacturing Optically Active Cyanohydrin

The present invention encompasses a method for manufacturing an optically active cyanohydrin.

This method comprises reacting a millipede-derived HNL with a reaction solution containing an aldehyde or ketone and hydrogen cyanide or a substance that produces cyanide ions in the reaction system to produce an optically active cyanohydrin.

The millipede-derived HNL is either the protein having HNL activity of the present invention, or the transformant of the present invention. The protein having HNL activity of the present invention may be a raw enzyme or purified enzyme. The transformant of the present invention may be in the form of the bacterial cells themselves or crushed cells or the like.

Apart from the fact that the millipede-derived HNL is either the protein having HNL activity of the present invention or the transformant of the present invention, the methods described in PTL 1 may be consulted with respect to the method for manufacturing an optically active cyanohydrin.

In the manufacturing method of the present invention, the aldehyde or ketone serving as the reaction substrate is a compound represented by Formula (1): $R^1$—(C=O)$R^2$ for example.

In the Formula (1), $R^1$ and $R^2$ are (i) hydrogen atoms, (ii) optionally substituted $C_{1-18}$ linear or branched saturated alkyl groups, or (iii) optionally substituted 5- to 22-member cyclic aromatic groups. However, $R^1$ and $R^2$ may not both be hydrogen atoms. When $R^1$ and $R^2$ are substituted alkyl groups in (ii) above, the substituents thereof are one or more amino groups, imino groups, hydroxy group, $C_{1-8}$ alkoxy groups, halogens, carboxyl groups, $C_{3-20}$ cycloalkyl groups, or aromatic groups with up to 22 carbon atoms optionally substituted with N, O or S hetero atoms (and when a substituent is a cyclic substituent, the substituent itself may also be substituted with one or more halogen, hydroxy groups, $C_{1-8}$ linear or branched alkyl groups, or $C_{2-8}$ linear or branched alkenyl groups). The aromatic groups of (iii) above may also be heteroaromatic groups in which up to 4 ring members are substituted with N, O and/or S. When $R^1$ and $R^2$ are substituted aromatic groups, moreover, the substituents are one or more amino groups, imino groups, hydroxy groups, $C_{1-8}$ alkoxy groups, allyloxy groups, halogens, carboxyl groups, or linear or branched saturated or unsaturated alkyl groups with up to 22 carbon atoms (wherein each aromatic group may be substituted with at least 2 substituents).

Hydrogen cyanide is used as a raw material for converting the aldehyde or ketone into an optically active cyanohydrin, and the method of supplying the hydrogen cyanide may be either a liquid supply method or a gas supply method. Moreover, not only hydrogen cyanide but also hydrocyanic acid (an aqueous solution of hydrogen cyanide, that is, prussic acid) may also be used in exactly the same way. A substance that produces cyanide ions (CN⁻) when added to the reaction system may also be used, and examples include hydrogen cyanide salts such as sodium cyanide and potassium cyanide, and cyanohydrins such as acetone cyanohydrin.

Considering that the optically active cyanohydrin produced by the enzyme reaction is likely to be racemized when a large quantity of water is present in the reaction system, and production efficiency is also lower in this case when an aldehyde or ketone with poor water-solubility is used as a raw material, an organic solvent that is insoluble or hardly soluble in water is preferred as the reaction solvent. This organic solvent is not particularly limited as long as it does not affect synthesis of the optically active cyanohydrin by the enzyme reaction, and it may be selected appropriately depending on the physical properties of the aldehyde and ketone raw materials used in the synthesis reaction and the physical properties of the cyanohydrin product. Specific examples include optionally halogenated, aliphatic or aromatic, linear, branched or cyclic, saturated or unsaturated hydrocarbon solvents, such as pentane, hexane, toluene, xylene and methylene chloride; optionally halogenated, aliphatic or aromatic, linear, branched or cyclic, saturated or unsaturated alcohol solvents, such as isopropyl alcohol, n-butanol, isobutanol, t-butanol, hexanol, cyclohexanol and n-amyl alcohol; optionally halogenated, aliphatic or aromatic, linear, branched or cyclic, saturated or unsaturated ether solvents, such as diethyl ether, dipropyl ether, diisopropyl ether, dibutyl ether and methyl-t-butyl ether; and optionally halogenated, aliphatic or aromatic, linear, branched or cyclic, saturated or unsaturated ester solvents, such as methyl formate, methyl acetate, ethyl acetate, butyl acetate and butyl propionate, which may be used alone or in combinations of multiple solvents. These organic solvents may also be saturated with pH 7 or lower aqueous buffers, such as citrate buffer, phosphate buffer, acetate buffer or the like.

The concentrate of the aldehyde or ketone in the reaction solvent is preferably 0.01 mM to 5 M, and the hydrogen cyanide or substance that produces cyanide ions can be used in the amount of 1 to 20 moles per 1 mole of the aldehyde or ketone, while the recombinant microbial cells may be used in an amount sufficient to produce at least 1 unit/mmol of enzyme activity relative to the aldehyde or ketone concentration for example. The enzyme activity of the cells can be calculated for example by suspending the cells in water or buffer solution, crushing them, and using the supernatant obtained by centrifugation to measure absorption changes at a wavelength of 249.6 nm when benzaldehyde is produced due to decomposition of the substrate by the enzyme using DL-mandelonitrile as the substrate.

The pH of the reaction solvent does not need to be adjusted when the organic solvent has not been saturated with an aqueous buffer, but when it has been saturated with an aqueous buffer, the pH of the aqueous buffer is adjusted to the range of 3 to 7, or preferably 3 to 6. The reaction temperature is preferably as low as possible within the range that produces the enzyme activity in order to suppress by-production of racemic cyanohydrin outside the enzyme reaction, and is normally 0° C. to 50° C., or preferably 10° C. to 45° C.

Once the reaction is complete, the cells are separated from the reaction solution to produce a reaction product solution. The target optically active cyanohydrin can be obtained by separating components other than the optically active cyanohydrin from the reaction product solution. The products are separated using ordinary techniques such as distillation separation, column chromatographic separation, extraction separation and the like. The solution may also be dehydrated at this time by addition of a dehydrating agent, and a stabilizer may also be added.

EXAMPLES

The present invention is explained in more detail below based on examples. However, these are only examples of the present invention, and the intent is not to limit the present example to these examples.

Methods for Measuring (R)-Mandelonitrile Synthesis Activity

200 µl of a reaction solution containing 0.4 U of HNL, 300 mM of citrate buffer (pH 4 to 5), 50 mM of benzaldehyde and 100 mM of KCN was reacted for 5 minutes at 30° C. to 35° C., and (R)-mandelonitrile was assayed by HPLC.

Example 1: Purification of HNL from Nedyopus tambanus tambanus (NttHNL)

Nedyopus tambanus tambanus (Attems) was collected at Toyama Prefectural University. A raw enzyme solution was extracted from the millipede, and NttHNL was purified as follows.

Ammonium sulfate was added to the raw enzyme solution to a saturation concentration of 35%, and the solution was adsorbed on HiTrap Butyl HP (GE Health Care), and eluted with an ammonium sulfate concentration gradient. This was desalted, and the NttHNL was adsorbed on ResourceQ, and eluted with a NaCl concentration gradient. This was then added to Superdex75 10/300 GL (GE Health Care), and eluted with PBS. The purified NttHNL exhibited (R)-mandelonitrile synthesis activity, with a specific activity value of 4700 U/mg.

The purified NttHNL was subjected to N-terminal amino acid sequence analysis and internal sequence analysis. As a result, an N-terminal amino acid sequence of EEEPLTXDKL and internal amino acid sequences of EEEP (I/L)TCDQ(I/L)PK, (I/L)QTQAVEVAK were obtained.

Example 2: Cloning of NttHNL Gene

Total RNA was extracted from Nedyopus tambanus tambanus with TRIzol (Invitrogen), and cDNA was synthesized with Gene Racer Kit (Invitrogen). Degenerate primers were designed from the N-terminal amino acid sequence and internal sequence of NttHNL, and a partial sequence of cDNA encoding for NttHNL was amplified by PCR. Degenerate Primer Sequences:

```
NttHNL-F:
                                        (SEQ ID NO: 25)
GARGARCCNHTNACNTGYGATAA

NttHNL-R:
                                        (SEQ ID NO: 26)
TTYTCNACNGCYTGNGTCTG
```

The amplified DNA was linked to pCR-blunt (Invitrogen), and the nucleotide sequence of the insert was determined. Next, the full nucleotide sequence of cDNA encoding for NttHNL was determined by performing 5'- and 3'-RACE using primers designed from the internal sequence.
Primer Sequences:

```
NttHNL-F1:
                                        (SEQ ID NO: 27)
GTTCCAGTTCCTCCGTTAGAAGATTTT

NttHNL-F2:
                                        (SEQ ID NO: 28)
CCCAGGCTGCAACTGCATTGGACATT

NttHNL-R1:
                                        (SEQ ID NO: 29)
CTCTGCAATTGCAGAACCATTGCACGTA

NttHNL-R2:
                                        (SEQ ID NO: 30)
CCATTTGGGGTGTTCAAATTAGTATATT
```

Next, the region encoding for NttHNL was amplified by PCR using gene-specific primers, and linked to pCR-blunt to determine the nucleotide sequence.

Gene-Specific Primer Sequences:

```
NttHNL-FW:
                                      (SEQ ID NO: 31)
ATGCTGTTTTACGTTTCGATTCTTCTAG

NttHNL-RV:
                                      (SEQ ID NO: 32)
TTAATAGAAAGCAAAACAACCATGGTG
```

Example 3: Homology Cloning of Millipede-Derived Hydroxynitrile Lyase Genes

Total RNA was prepared by the methods described above from one individual each of *Nedyopus tambanus mangaesinus* (Attems), *Oxidus gracilis* (C. L. Koch), *Parafontaria falcifera* (Verhoeff), *Parafontaria laminata* (Attems), *Parafontaria tonominea* (Attems) and a *Riukiaria* species, and cDNA was synthesized using a Gene Racer Kit or SMART RACE cDNA Amplification Kit (Clontech Laboratories, Inc.). PCR was performed using degenerate primers designed based on the homologous sequences of ChuaHNL and NttHNL, to thereby amplify partial sequences of each millipede-derived HNL gene.

Degenerate Primer Sequences:

```
HNL-FW:
                                      (SEQ ID NO: 17)
CTGCAACTGCATTGGAMATTCAAGG

HNL-RV:
                                      (SEQ ID NO: 18)
ATGAATCTTRTCRCCGTTTGGAAC
```

Next, the full-length nucleotide sequences of cDNA encoding for each millipede-derived HNL were determined by performing 5'- and 3'-RACE using primers designed based on the partial sequences.

Primer Sequences:

```
NtmHNL-F1:
                                      (SEQ ID NO: 33)
TGGTGGACCTAATAACTCCGCCATA

NtmHNL-F2:
                                      (SEQ ID NO: 34)
CCCAGATGGAAGTTCATATTGCGCTTA

NtmHNL-R1:
                                      (SEQ ID NO: 35)
GAGTGGGTCGGTTCCATTGTTATTAT

NtmHNL-R2:
                                      (SEQ ID NO: 36)
GCCATTGCACGTATAAGCGCAATAT

OgraHNL-F1:
                                      (SEQ ID NO: 37)
CGTTGGTGGTCCTAATAATTCAGCTAT OgraHNL-F2:
                                      (SEQ ID NO: 38)
CACCAATCTGAACACTCCAAATGGAA OgraHNL-R1:
                                      (SEQ ID NO: 39)
GGATCGGTTCCGTTGTTGTTATTA OgraHNL-R2:
                                      (SEQ ID NO: 40)
CGTATAGGCGCAATAGGAGCTTCCATT PfalHNL-F1:
                                      (SEQ ID NO: 41)
GACTTCACCATTGGTTCTGATTCTAT PfalHNL-F2:
                                      (SEQ ID NO: 42)
CCCCAAGGTGCCAACTATTGTGCATA PfalHNL-R1:
                                      (SEQ ID NO: 43)
CAGCCTGACGTTGTGTAGCTGATATGT PfalHNL-R2:
                                      (SEQ ID NO: 44)
CGGGACCATTGCAAGAGTATGCACAAT PlamHNL-F1:
                                      (SEQ ID NO: 45)
ATTCAAGGAACTCACATAACAATAAATGACTTC PlamHNL-F2:
                                      (SEQ ID NO: 46)
ATGAATCTTGTCACCGTTTGGAACTGATCG PlamHNL-R1:
                                      (SEQ ID NO: 47)
GAGTTGTTTAGGCGATATGTATCCAGTATTC PlamHNL-R2:
                                      (SEQ ID NO: 48)
GAGTTGTTTAGGCGATATGTATCCAGTATTC Pton1HNL-F1:
                                      (SEQ ID NO: 49)
GGTCCCGATGCTATGACGGCCTATTT Pton1HNL-F2:
                                      (SEQ ID NO: 50)
GGTGCCAACTATTGTGCATACTTTT Pton1HNL-R1:
                                      (SEQ ID NO: 51)
GCCTGGAGTTGTTGAGGCGATATGTA Pton1HNL-R2:
                                      (SEQ ID NO: 52)
GGGACCATTGCAAAAGTATGCACAATA RspHNL-F1:
                                      (SEQ ID NO: 53)
CCGGGGCAAAACAGGTTTGGTA RspHNL-F2:
                                      (SEQ ID NO: 54)
GGGTGCCAACTATTGCGCATACTCTT RspHNL-R1:
                                      (SEQ ID NO: 55)
GCCAGTATTGGAAGTGCATTTGTATT RspHNL-R2:
                                      (SEQ ID NO: 56)
CAGGGGATCATCGAGGTCGACATATT PtokHNL-F1:
                                      (SEQ ID NO: 91)
GGACAGCCTTTTCGACTAATTGTGAT PtokHNL-F2:
                                      (SEQ ID NO: 92)
CCCAAGGTGCCAACTACTGTGCATA PtokHNL-R1:
                                      (SEQ ID NO: 93)
GCCTGGAGTTGTTGAGGCGATATGTAT PtokHNL-R2:
                                      (SEQ ID NO: 94)
GCAAGAGTAGCCTATGCACAGTAGTTG
```

Pton2HNL-F1:
CCGATGGTCTGACAGCCTATTTGACTA
(SEQ ID NO: 95)

Pton2HNL-F2:
CCCCAAGGTGCCAACTACTGTGCATA
(SEQ ID NO: 96)

Pton2HNL-R1:
GGCGATATGTATCCAGTATTCGTAGTGCA
(SEQ ID NO: 97)

Pton2HNL-R2:
CGGGACCATTGCAAGAGTATGCACAGT
(SEQ ID NO: 98)

Pton3HNL-F1:
CTGACAGCCTATTTGACTAATTGTGAT
(SEQ ID NO: 99)

Pton3HNL-F2:
GCATACTCTTGCAATGGTTCCGAAA
(SEQ ID NO: 100)

Pton3HNL-R1:
GCCTGGAGTTGTTGAGGCGATATGTAT
(SEQ ID NO: 101)

Pton3HNL-R2:
CGGAACCATTGCAAGAGTATGCACA
(SEQ ID NO: 102)

RssHNL-F1:
GACTTCCTCATCGCTCCTGATTGTAT
(SEQ ID NO: 103)

RssHNL-F2:
CGTCGAGGATCCCAAGGGTGCCAA
(SEQ ID NO: 104)

RssHNL-R1:
GCCAGCTATATTGGAAGTGCATTT
(SEQ ID NO: 105)

RssHNL-R2:
CCATCGCAAGAGTATGCGCAATAGTT
(SEQ ID NO: 106)

Next, the coding regions of each hydroxynitrile lyase were amplified using gene-specific primers, the PlamHNL was linked to the T-Vector pMD20 vector (Takara Bio Inc.) and the others to pCR-blunt, and the nucleotide sequences were determined.

Gene-Specific Primer Sequences:

NtmHNL-FW:
ATGCTGTTTTACGTCTCGATTCTTC
(SEQ ID NO: 57)

NtmHNL-RV:
TCAATAGAAAGCAAAACAGCCATGG
(SEQ ID NO: 58)

OgraHNL-FW:
ATGTTGTACTACGTTTCAATACTTT
(SEQ ID NO: 59)

OgraHNL-RV:
CTAATAGAAAGCAAAACAGCCATGG
(SEQ ID NO: 60)

PfalHNL-FW:
ATGACTTCGATCATTTTCCTCACG
(SEQ ID NO: 61)

PfalHNL-RV:
TTAGTAATAGAGAGGACAGAAAGGG
(SEQ ID NO: 62)

PlamHNL-FW:
ATGACTTCGATCATTCTCCTCATGACTG
(SEQ ID NO: 63)

PlamHNL-RV:
GCTTAATTCAATTGCACTTTAATTTTTATATC
(SEQ ID NO: 64)

Pton1HNL-FW:
ATGACTTCAATCATTCTCCTCTTGG
(SEQ ID NO: 65)

Pton1HNL-RV:
TTAGTAATAGAGAGGACAGAAAGGGTG
(SEQ ID NO: 66)

RspHNL-FW:
ATGACTTCGATCATGTTCAGCCTG
(SEQ ID NO: 67)

RspHNL-RV:
TTAGCTATAGAAGGGGCAGATAGGG
(SEQ ID NO: 68)

PtokHNL-FW:
ATGACTTCGATCATTCTCCTCACG
(SEQ ID NO: 107)

PtokHNL-RV:
TTAGTAATAGAGGGGACAGAAAAGG
(SEQ ID NO: 108)

Pton2HNL-FW:
ATGACTTCGATCATTCTCCTCACG
(SEQ ID NO: 109)

Pton2HNL-RV:
TTAGTAATAGAGAGGACAGTAAAGGTG
(SEQ ID NO: 110)

Pton3HNL-FW:
ATGACTTCGATCATTCTCCTCACG
(SEQ ID NO: 111)

Pton3HNL-RV:
TTAGTAATAGAGAGGACAGTAAAGG
(SEQ ID NO: 112)

RssHNL-FW:
ATGACTTCGATCATGCTCTGTTTAAC
(SEQ ID NO: 113)

RssHNL-RV:
TTAGCTATAGAAGGGGCAGAAAGGG
(SEQ ID NO: 114)

The abbreviations are defined as follows.

ChuaHNL: Hydroxynitrile lyase from *Chamberlinius hualienensis*
NttHNL: Hydroxynitrile lyase from *Nedyopus tambanus tambanus* (SEQ ID NO:1)
NtmHNL: Hydroxynitrile lyase from *Nedyopus tambanus mangaesinus* (SEQ ID NO:3)
OgraHNL: Hydroxynitrile lyase from *Oxidus gracilis* (SEQ ID NO:5)
PfalHNL: Hydroxynitrile lyase from *Parafontaria falcifera* (SEQ ID NO:7)
Pton1HNL: Hydroxynitrile lyase from *Parafontaria tonominea* (SEQ ID NO:9)
PlamHNL: Hydroxynitrile lyase from *Parafontaria laminata* (SEQ ID NO:11)
RspHNL: Hydroxynitrile lyase from one species of *Riukiaria* (SEQ ID NO:13)
PtokHNL: Hydroxynitrile lyase from *Parafontaria tokaiensis* (SEQ ID NO:83)
Pton2HNL: Hydroxynitrile lyase from *Parafontaria tonominea* (SEQ ID NO:85)

Pton3HNL: Hydroxynitrile lyase from *Parafontaria tonominea* (SEQ ID NO:87)
RssHNL: Hydroxynitrile lyase from a *Riukiara* species (SEQ ID NO:89)

The respective amino acid sequences are represented by SEQ ID NOS:1, 3, 5, 7, 9, 11, 13, 83, 85, 87 and 89.

The corresponding nucleotide sequences are represented by SEQ ID NOS:2, 4, 6, 8, 10, 12, 14, 84, 86, 88 and 90. The homologies of the respective amino acid sequences are summarized in Table 1. It has been shown that genes encoding for millipede-derived hydroxynitrile lyase having at least 41% homology with ChuaHNL can be cloned by this method.

TABLE 1

Homology (%) among millipede-derived hydroxynitrile lyases

|  | ChuaHNL | NttHNL | NtmHNL | OgraHNL | PfalHNL | PtokHNL |
|---|---|---|---|---|---|---|
| ChuaHNL | 100 | 64 | 65 | 66 | 47 | 46 |
| NttHNL | 64 | 100 | 93 | 85 | 52 | 49 |
| NtmHNL | 65 | 93 | 100 | 85 | 50 | 50 |
| OgraHNL | 66 | 85 | 85 | 100 | 51 | 49 |
| PfalHNL | 47 | 52 | 50 | 51 | 100 | 82 |
| PtokHNL | 46 | 49 | 50 | 49 | 82 | 100 |
| PtonHNL | 48 | 52 | 51 | 51 | 86 | 86 |
| Pton2HNL | 47 | 50 | 50 | 49 | 85 | 94 |
| Pton3HNL | 46 | 51 | 49 | 49 | 85 | 91 |
| PlamHNL | 46 | 50 | 49 | 48 | 81 | 90 |
| RspHNL | 41 | 43 | 44 | 46 | 65 | 66 |
| RssHNL | 43 | 45 | 45 | 44 | 68 | 70 |

|  | Pton1HNL | Pton2HNL | Pton3HNL | PlamHNL | RspHNL | RssHNL |
|---|---|---|---|---|---|---|
| ChuaHNL | 48 | 47 | 46 | 46 | 41 | 43 |
| NttHNL | 52 | 50 | 51 | 50 | 43 | 45 |
| NtmHNL | 51 | 50 | 49 | 49 | 44 | 45 |
| OgraHNL | 51 | 49 | 49 | 48 | 46 | 44 |
| PfalHNL | 86 | 85 | 85 | 81 | 65 | 68 |
| PtokHNL | 86 | 94 | 91 | 90 | 66 | 70 |
| PtonHNL | 100 | 87 | 87 | 84 | 68 | 70 |
| Pton2HNL | 87 | 100 | 96 | 89 | 66 | 70 |
| Pton3HNL | 87 | 96 | 100 | 88 | 67 | 70 |
| PlamHNL | 84 | 89 | 88 | 100 | 67 | 72 |
| RspHNL | 68 | 66 | 67 | 67 | 100 | 89 |
| RssHNL | 70 | 70 | 70 | 72 | 89 | 100 |

Example 4: Cloning of ChuaHNL Gene

Total RNA was prepared by the methods given in Example 3 from *Chamberlinius hualienensis*, and cDNA was synthesized. The region encoding for ChuaHNL was amplified using primers, and linked to pCR-blunt.

Primer Sequences:

```
ChuaHNL-FW:
                                         (SEQ ID NO: 69)
ggatccATGTTGAGTTCACTAGTAGTAACAGTAA ChuaHNL-RV:
                                         (SEQ ID NO: 70)
aagcttAGTAAAAAGCAAAGCAACCGTGGGTTTCG
```

Example 5: Expression of Hydroxynitrile Lyase Genes in Cultured Insect Cells The millipede-derived hydroxynitrile lyase genes described above were expressed with a Baculovirus-insect cell expression system. Insert DNA was prepared by PCR using the various primers and Tks Gflex DNA polymerase, with each of the plasmid DNAs obtained in Examples 2, 3 and 4 as the templates.

Primer Sequences:

```
IFSf-NttHNL-FW:
                                         (SEQ ID NO: 71)
gggcgcggatccATGCTGTTTTACGTTTCGATTC IFSf-NttHNL-RV:
                                         (SEQ ID NO: 72)
acttctcgacaagcttTTAATAGAAAGCAAAACAACCATGG IFSf-NtmHNL-FW:
                                         (SEQ ID NO: 73)
catcgggcgcggatccATGCTGTTTTACGTTTCGATTCTTC
```

-continued
```
IFSf-NtmHNL-RV:
                                         (SEQ ID NO: 74)
acttctcgacaagcttTCAATAGAAAGCAAAACAGCCATGG IFSf-OgraHNL-FW:
                                         (SEQ ID NO: 75)
catcgggcgcggatccATGTTGTACTACGTTTCAATAC IFSf-OgraHNL-RV:
                                         (SEQ ID NO: 76)
acttctcgacaagcttCTAATAGAAAGCAAAACAGCCATG IFSf-PfalHNL-FW:
                                         (SEQ ID NO: 77)
catcgggcgcggatccATGACTTCGATCATTTTCCTCACG IFSf-PfalHNL-RV:
                                         (SEQ ID NO: 78)
acttctcgacaagcttTTAGTAATAGAGAGGACAGAAAGGG IFSf-Pton1HNL-FW:
                                         (SEQ ID NO: 79)
catcgggcgcggatccATGACTTCAATCATTCTCCTCTTG IFSf-Pton1HNL-RV:
                                         (SEQ ID NO: 80)
acttctcgacaagcttTTAGTAATAGAGAGGACAGAAAGGGTG
```

-continued

IFSf-RspHNL-FW:
(SEQ ID NO: 81)
catcgggcgcggatccATGACTTCGATCATGTTCAGCCTG

IFSf-RspHNL-RV:
(SEQ ID NO: 82)
acttctcgacaagcttTTAGCTATAGAAGGGGCAGATAGGG

IFSf-PtokHNL-FW:
(SEQ ID NO: 115)
catcgggcgcggatccATGACTTCGATCATTCTCCTCACG

IFSf-PtokHNL-RV:
(SEQ ID NO: 116)
acttctcgacaagcttTTAGTAATAGAGGGGACAGAAAAGG

IFSf-Pton2HNL-FW:
(SEQ ID NO: 117)
catcgggcgcggatccATGACTTCGATCATTCTCCTCACG

IFSf-Pton2HNL-RV:
(SEQ ID NO: 118)
acttctcgacaagcttTTAGTAATAGAGAGGACAGTAAAGGTG

IFSf-Pton3HNL-FW:
(SEQ ID NO: 119)
catcgggcgcggatccATGACTTCGATCATTCTCCTCACG

IFSf-Pton3HNL-RV:
(SEQ ID NO: 120)
acttctcgacaagcttTTAGTAATAGAGAGGACAGTAAAGG

IFSf-RssHNL-FW:
(SEQ ID NO: 121)
catcgggcgcggatccATGACTTCGATCATGCTCTGTTTA

IFSf-RssHNL-RV:
(SEQ ID NO: 122)
acttctcgacaagcttttagcTATAGAAGGGGCAGAAAGGG

Using an In-Fusion HD cloning kit (Takara Bio Inc.), the insert DNA was linked to the BamHI-HindIII site of a pFastbac1 vector (Invitrogen). Using a KOD-Plus-Mutagenesis Kit (Toyobo Co., Ltd.), a sequence coding for a His tag was also introduced immediately below the signal peptide cleavage site of each hydroxynitrile lyase. The signal peptide cleavage sites were predicted using SignalP (Nature Methods, 8:785-786, 2011). The absence of mutations due to PCR was then confirmed by sequencing the insert. Each of the resulting plasmids was introduced into E. coli DH10BAC, and recombinant bacmid DNA was extracted from the transformants with a QIAGEN Plasmid Mini Kit (Qiagen). The recombinant bacmid DNA was then transfected into Sf9 cells using X-tremeGENE 9 DNA transfection reagents (Roche). The recombinant Baculovirus was collected and transfected again into Sf9 cells to amplify the recombinant Baculovirus, and then transfected again into Sf9 cells to amplify the recombinant Baculovirus. The titer of the recombinant Baculovirus was calculated by comparing each sample with Baculovirus DNA of known titer by real-time PCR using ie1 gene amplification primers (Biotechnol. Prog., 20:354-360, 2004). The recombinant Baculovirus DNA was prepared using NucleoSpin Virus (Takara Bio Inc.).

Secretory expression of each millipede-derived HNL was achieved by transfecting each recombinant Baculovirus into Sf9 cells ($1.5 \times 10^6$ cells/mL) at a multiple infection degree of 1. 72 hours after transfection of the recombinant Baculovirus, the cells were removed by centrifugation, and the culture supernatant was collected. The culture supernatant was diluted with an equal amount of 20 mM HEPES-NaOH (pH 8.0), and added to complete Histag Purification resin (Roche). Each HNL adsorbed on the carrier was eluted with 10 mM HEPES-NaOH (pH 8.0) containing 0.1 M imidazole and 0.1 M NaCl. After elution, ammonium sulfate was added to a saturation concentration of 30%, and the resulting solution was added to HiTrap Butyl HP (GE Health Care), and then eluted with an ammonium sulfate concentration gradient (30% to 0%). After being desalted, each HNL was adsorbed on ResourceQ, and eluted with a NaCl concentration gradient (0 to 300 mM). The purity of the purified HNL was analyzed by SDS-PAGE.

The protein concentration was measured with a TaKaRa BCA Protein Assay Kit (Takara Bio Inc.), using fetal bovine serum albumin as the standard. Each hydroxynitrile lyase exhibited (R)-mandelonitrile synthesis activity (see Table 2a).

Example 6: Expression of Millipede-Derived Hydroxynitrile Lyase Genes in E. coli Expression of ChuaHNL, NttHNL, NtmHNL, OgraHNL, PfalHNL, Pton1HNL, PlamHNL, RspHNL, PtokHNL, Pton2HNL, Pton3HNL and RssHNL genes was attempted in E. coli BL21 (DE3) and SHuffle T7 (New England Biolabs).

In order to use the region excluding the signal sequence as the insert DNA, PCR was performed with the various primers and Tks Gflex DNA polymerase using each plasmid DNA obtained in Example 3 as the template. The insert DNA was attached with an In-Fusion HD cloning kit (Takara Bio Inc.) to the NdeI-HindIII site of a pET28 vector (Clontech Laboratories, Inc.) so that it would be expressed as a His-tag fusion protein. However, the PlamHNL was attached to the BamHI-HindIII site of a pET28 vector. The absence of mutations was then confirmed by sequencing the insert by PCR. Each of the resulting plasmids was introduced into E. coli BL21 (DE3) or SHuffle T7 (New England Biolabs). The transformants were cultured at 30° C. for 16 hours in LB medium containing kanamycin, transplanted into TB auto-induction medium, and cultured for 24 hours at 26° C. The cells were collected and crushed by ultrasound, and the insoluble matter was precipitated by centrifugation to obtain a cell-free extract.

Hydroxynitrile lyase gene expression was analyzed by analyzing mandelonitrile decomposition activity. That is, the cell-free extract was added to 0.1 M citrate buffer containing 2 mM (R,S)-mandelontrile, and benzaldehyde production was monitored at 280 nm.

None of the hydroxynitrile lyase genes was expressed with the E. coli BL21 (DE3). However, expression of the NtmHNL, OgraHNL, Pton2HNL, Pton3HNL and PlamHNL genes was confirmed with the E. coli SHuffle T7 (see Table 2a).

TABLE 2a

| | Millipede | Sf9 cells | E. coli SHuffle T7 |
|---|---|---|---|
| ChuaHNL | 7420 U/mg (Dadashipour et al., 2015) | Not tested | Not expressed |
| NttHNL | 4700 U/mg | 2731 U/mg | Not expressed |
| NtmHNL | — | 2916 U/mg | 1016 U/mg |
| OgraHNL | — | 2225 U/mg | 1779 U/mg |
| PfalHNL | — | Expressed | Not expressed |
| PtokHNL | — | Expressed | Not expressed |
| Pton1HNL | — | Expressed | Not expressed |
| Pton2HNL | — | Expressed | 3371 U/mg |
| Pton3HNL | — | Expressed | 2140 U/mg |
| PlamHNL | 1320 U/mg | | 1156 U/mg |
| RspHNL | — | Expressed | Not expressed |
| RssHNL | — | Expressed | Not expressed |

In the following Examples 7 to 13, the expressed NtmHNL, OgraHNL, PlamHNL and Pton3HNL were purified, and their enzymatic chemistries were elucidated.

Example 7: Purification of OgraHNL

OgraHNL was purified as follows. A cell-free extract prepared by the methods of Example 6 was added to HisTrap HP (GE Health Care). OgraHNL was eluted with an imidazole concentration gradient (20 to 500 mM). The fraction with the eluted OgraHNL was collected, and added to ResourceQ (GE Health Care). OgraHNL was eluted with a sodium chloride concentration gradient (0 to 300 mM). The fraction with the eluted OgraHNL was collected, and concentrated with an Amicon Ultra-4 centrifugal filter unit (Millipore). This was then added to Superdex75 10/300 GL (GE Health Care), and eluted with 10 mM HEPES-NaOH (pH 8.0) containing 0.1 M NaCl. The purification steps are summarized in Table 2b.

The purified OgraHNL exhibited (R)-mandelonitrile synthesis activity, with a specific activity value of 1779 U/mg, roughly matching the 2225 U/mg (see Table 2a) specific activity of OgraHNL expressed in cultured insect cells.

TABLE 2

OgraHNL purification steps

| Purification step | Activity (U) | Protein, mg | Specific activity, U/mg | Yield (%) | Purification fold |
|---|---|---|---|---|---|
| Cell-free extract | 651.3 | 2505 | 0.26 | 100 | 1 |
| HisTrap HP | 653.1 | 2.1 | 311 | 100 | 1196 |
| Resource Q | 260.1 | 0.18 | 1445 | 40 | 5558 |
| Superdex 75 | 105 | 0.059 | 1779 | 16 | 6842 |

Example 8: Effect of Temperature and pH on OgraHNL

(a) Optimum Temperature and Temperature Stability

Figure 2A:
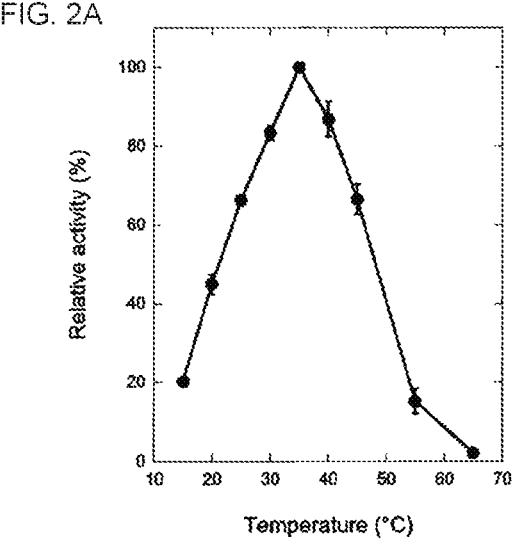
FIGS. 2A-2D show the effects of heat and pH on OgraHNL purified from *E. coli*.

The optimum temperature and temperature stability of OgraHNL were investigated. An enzyme reaction was performed for 5 minutes at each temperature with 200 µl of a reaction solution containing 0.4 U of OgraHNL, 300 mM of citrate buffer (pH 4.2), 50 mM of benzaldehyde and 100 mM of KCN. (R)-mandelonitrile was quantified by HPLC, with the measurement results shown in FIG. 2A. The optimum temperature of OgraHNL was estimated to be 35° C.

Figure 2B:
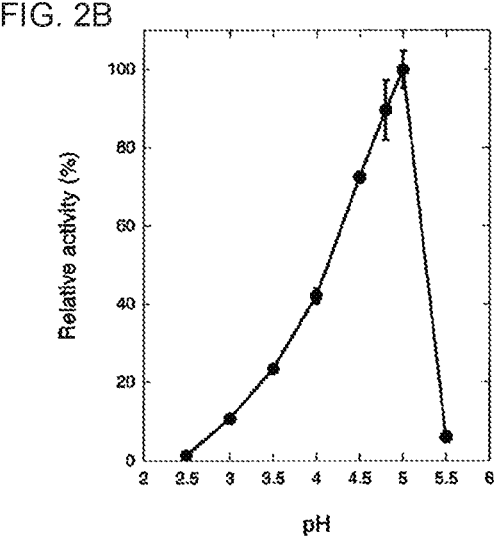
Figure 2C:
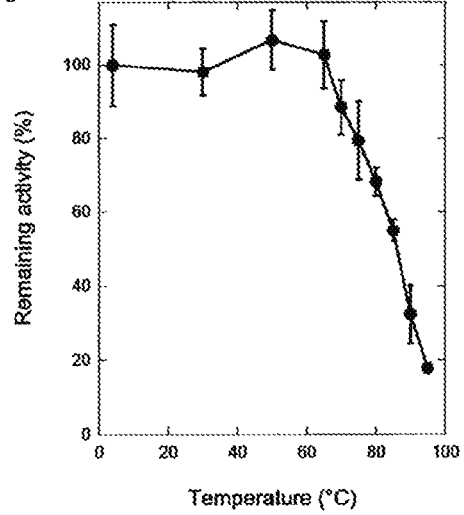

After 60 minutes of heating at each temperature, residual activity was measured to test temperature stability. The results are shown in FIG. 2C. OgraHNL maintained its activity even after 1 hour of heating at 65° C., and had 18% residual activity even after 1 hour of heating at 95° C. ChuaHNL, which is reported to be the most stable of known HNLs, is described as maintaining 100% activity even after 1 hour of heating at 65° C., but is inactivated by 1 hour of heating at 90° C. (Dadashipur et al., Proc. Natl. Acad. Sci. USA. 112, 10605-10610 (2015), NPL 1). Thus, this shows that OgraHNL has even greater thermal stability than the HNL described in NPL 1.

(b) Optimum pH and pH Stability

The optimum pH and pH stability of OgraHNL were investigated. An enzyme reaction was performed for 5 minutes at each temperature using 200 µl of a reaction solution containing 0.4 U of OgraHNL, 300 mM of citrate buffer (pH 2.5 to 5.5), 50 mM of benzaldehyde and 100 mM of KCN. (R)-mandelonitrile was then quantified by HPLC. The measurement results are shown in FIG. 2B. The optimum pH of OgraHNL was estimated to be 5.0.

Figure 2D:
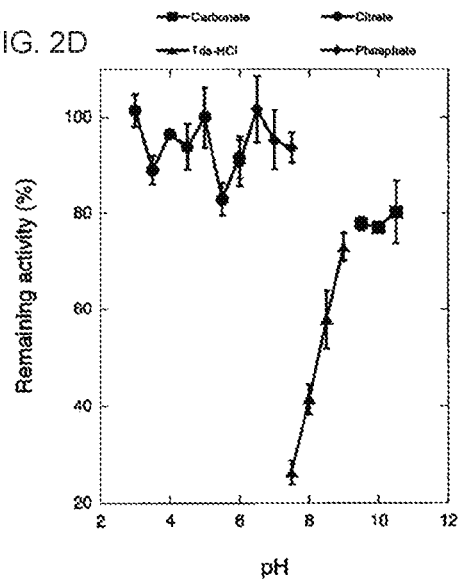

This was incubated for 60 minutes at 25° C. in each buffer, and residual activity was measured to investigate pH stability. The measurement results are shown in FIG. 2D. OgraHNL was stable within a pH range of 3 to 10.5. However, it was shown to be unstable in Tris-HCl buffer.

Example 9: Purification of NtmHNL

NtmHNL was purified as follows. A cell-free extract prepared by the methods of Example 6 was added to HisTrap HP (GE Health Care). NtmHNL was eluted with an imidazole concentration gradient (20 to 500 mM). The fraction with the eluted NtmHNL was collected, and added to ResourceQ (GE Health Care). NtmHNL was eluted with a sodium chloride concentration gradient (0 to 300 mM). The purification steps are summarized in Table 3. The purified NtmHNL exhibited (R)-mandelonitrile synthesis activity, with a specific activity value of 1016 U/mg.

TABLE 3

NtmHNL purification steps

| Purification step | Activity (U) | Protein, mg | Specific activity, U/mg | Yield (%) | Purification fold |
|---|---|---|---|---|---|
| Cell-free extract | 2767.6 | 4203.4 | 0.7 | 100 | 1 |
| HisTrap HP | 2548.9 | 5.7 | 447.2 | 92.1 | 679.2 |
| Resource Q | 1118.1 | 1.1 | 1016.4 | 40.4 | 1543.8 |

Example 10: Effects of Temperature and pH on NtmHNL

(a) Optimum Temperature and Temperature Stability

The optimum temperature and temperature stability of NtmHNL were investigated. An enzyme reaction was performed for 5 minutes at each temperature with 200 µl of a reaction solution containing 0.4 U of NtmHNL, 300 mM of citrate buffer (pH 4.2), 50 mM of benzaldehyde and 100 mM of KCN. (R)-mandelonitrile was quantified by HPLC, with the measurement results shown in FIG. 3A. The optimum temperature of NtmHNL was estimated to be 30° C.

(b) Optimum pH

The optimum pH and pH stability of NtmHNL were investigated. An enzyme reaction was performed for 5 minutes at each temperature using 200 µl of a reaction solution containing 0.4 U of NtmHNL, 300 mM of citrate buffer (pH 2.5 to 5.5), 50 mM of benzaldehyde and 100 mM of KCN. (R)-mandelonitrile was then quantified by HPLC. The measurement results are shown in FIG. 3B. The optimum pH of NtmHNL was estimated to be 4.8.

Example 11: Purification of PlamHNL

PlamHNL was purified as follows. A cell-free extract prepared by the methods of Example 6 was added to Ni Sepharose 6 FastFlow (GE Health Care). PlamHNL was eluted with 20 mM KPB (pH 8.0) containing 100 mM of imidazole and 500 mM of sodium chloride. The purified PlamHNL exhibited (R)-mandelonitrile synthesis activity, with a specific activity value of 1156 U/mg.

Example 12: Purification of Pton3HNL from Recombinant E. coli

Pton3HNL was purified as follows. A cell-free extract prepared by the methods of Example 6 was supplied to HisTrap HP (GE Health Care), and eluted with an imidazole concentration gradient (20 to 500 mM). The fraction with the eluted Pton3HNL was collected, supplied to ResourceQ (GE Health Care), and eluted with a sodium chloride concentration gradient (0 to 300 mM). The fraction with the eluted Pton3HNL was collected, and used as the purified enzyme.

The purified Pton3HNL exhibited (R)-mandelonitrile synthesis activity, with a specific activity value of 2140 U/mg.

Example 13: Effects of Temperature and pH on Pton3HNL

(a) Optimum Temperature and Temperature Stability

Figure 11A:
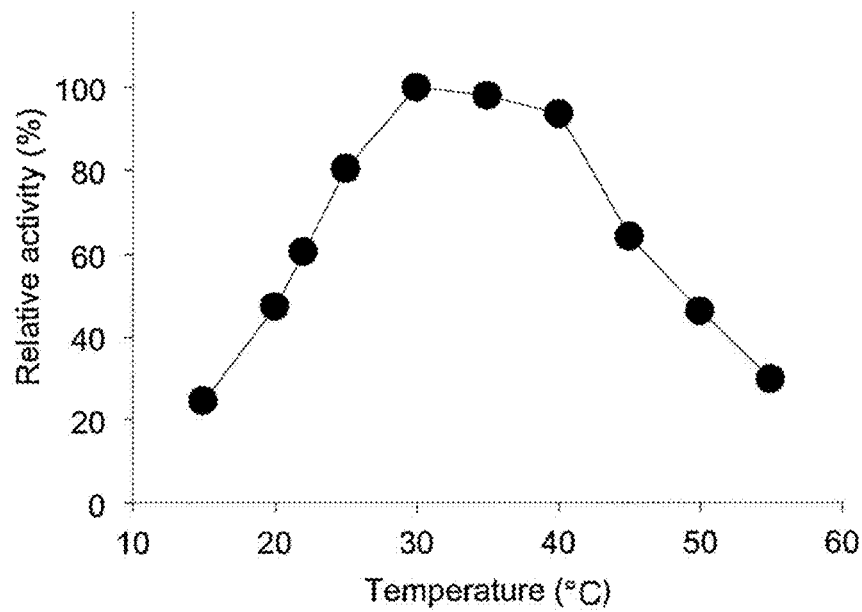
FIG. 11A shows test results for optimum temperature for Pton3HNL.

The optimum temperature and temperature stability of Pton3HNL were investigated. An enzyme reaction was performed for 5 minutes at each temperature with 200 μl of a reaction solution containing 0.4 U of Pton3HNL, 300 mM of citrate buffer (pH 4.2), 50 mM of benzaldehyde and 100 mM of KCN. (R)-mandelonitrile was quantified by HPLC, with the measurement results shown in FIG. 11A. The optimum temperature of Pton3HNL was estimated to be 30° C.

Figure 11B:
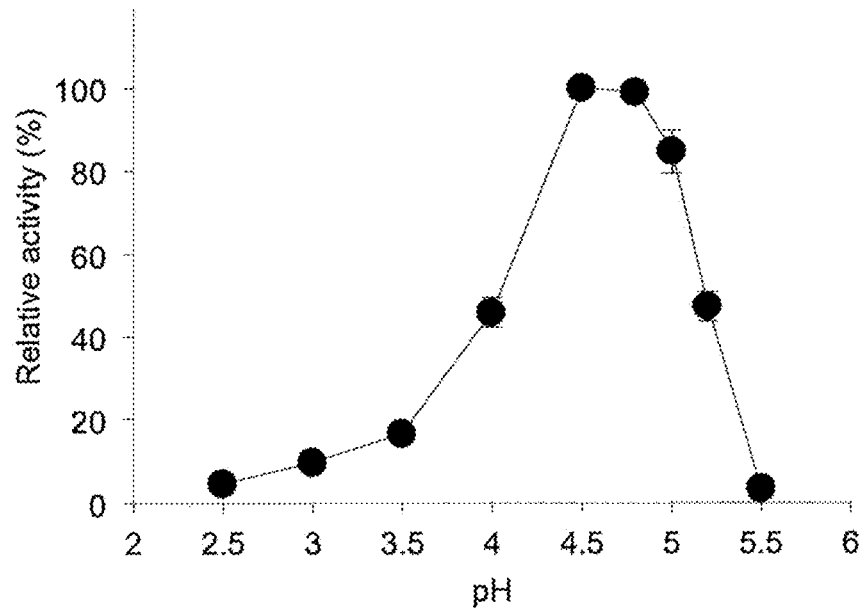
FIG. 11B shows test results for optimum pH for Pton3HNL.
Figure 11C:
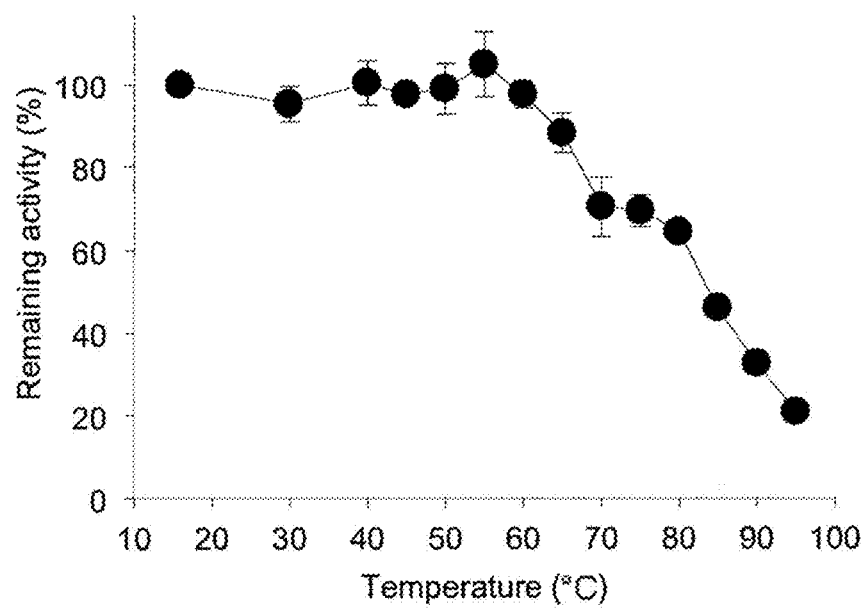
FIG. 11C shows test results for temperature stability of Pton3HNL.

After 60 minutes of heating at each temperature, residual activity was measured to test temperature stability. The results are shown in FIG. 11C. Pton3HNL maintained its activity even after 1 hour of heating at 60° C., and had 18% residual activity even after 1 hour of heating at 95° C.

(b) Optimum pH and pH Stability

The optimum pH and pH stability of Pton3HNL were investigated. An enzyme reaction was performed for 5 minutes at each temperature using 200 μl of a reaction solution containing 0.4 U of Pton3HNL, 300 mM of citrate buffer (pH 2.5 to 5.5), 50 mM of benzaldehyde and 100 mM of KCN. (R)-mandelonitrile was then quantified by HPLC. The measurement results are shown in FIG. 11B. The optimum pH of Pton3HNL was estimated to be 4.5.

Figure 11D:
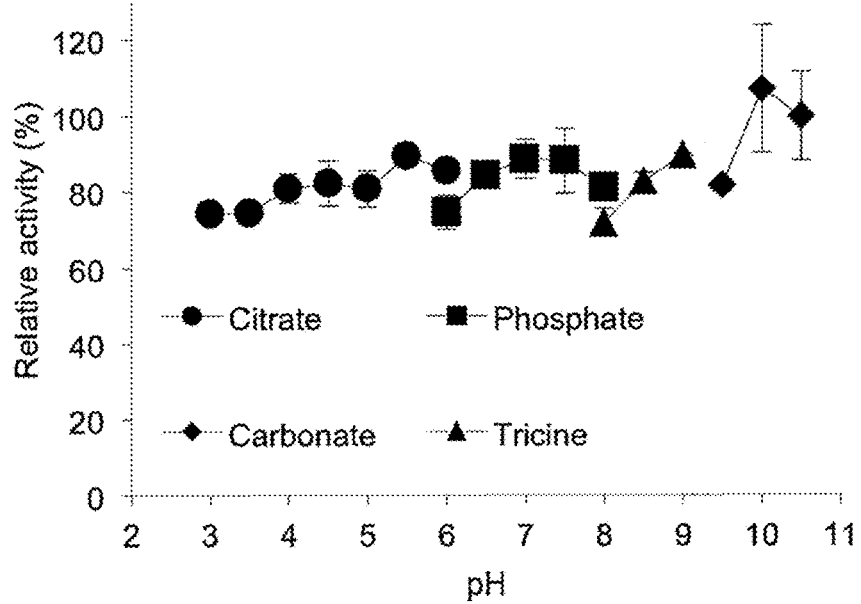
FIG. 11D shows test results for pH stability of Pton3HNL.

This was incubated for 60 minutes at 25° C. in each buffer, and residual activity was measured to investigate pH stability. The measurement results are shown in FIG. 11D. Pton3HNL was stable within a pH range of 3 to 10.5.

Example 14

Production of (R)-Mandelonitrile Using Recombinant E. coli

E. coli Shuffle expressing Pton3HNL was used to synthesize an optically active cyanohydrin by a whole cell reaction in an aqueous solution. Cells were collected from 0.8 mL of culture solution and suspended in 150 μL of 0.4 M citrate buffer (pH 3.0), 10 μL of 1 M benzaldehyde and 20 μL of 1M KCN were added, and the mixture was incubated for 5 minutes at 22° C. When the reaction product was extracted and analyzed by HPLC as described above, the enantiomeric excess (ee) was found to be 97.6% as shown in FIGS. 12A-12B.

Figure 12A:
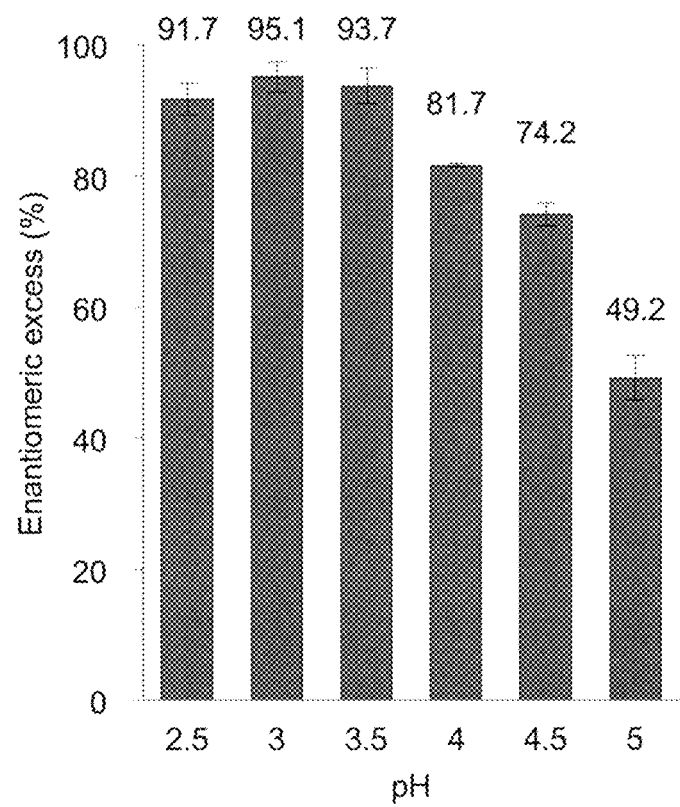
FIG. 12A shows results for (pH-dependent) production of (R)-mandelonitrile in Example 14.
Figure 12B:
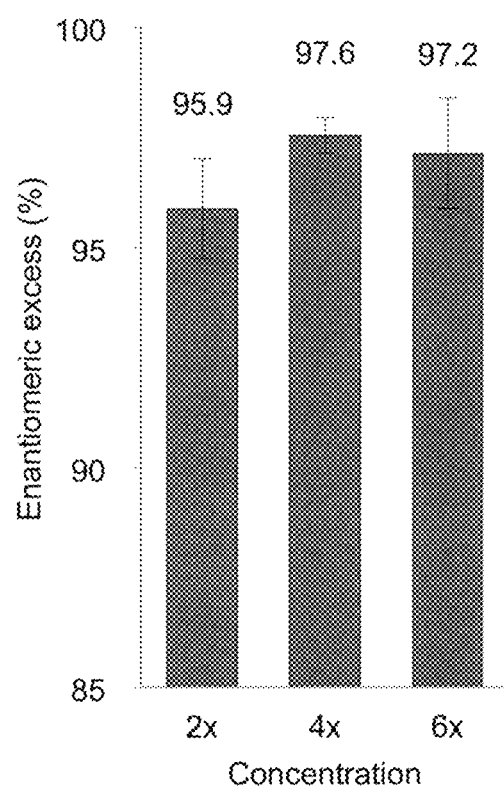
FIG. 12B shows results for (concentration-dependent) production of (R)-mandelonitrile in Example 14.

The results with the pH varied from 2.5 to 5.0 are shown in FIG. 12A, while FIG. 12B shows the results with the cell concentration varied from 2× to 4× to 6×.

INDUSTRIAL APPLICABILITY

Since optically active cyanohydrins are important intermediates in the manufacture of drugs and fine chemicals, the present invention is useful in fields related to the manufacture of drugs and fine chemicals.

Sequence Table Free Text

SEQ ID NO:1: NttHNL protein
SEQ ID NO:2: NttHNL gene
SEQ ID NO:3: NtmHNL protein
SEQ ID NO:4: NtmHNL gene
SEQ ID NO:5: OgraHNL protein
SEQ ID NO:6: OgraHNL gene
SEQ ID NO:7: PfalHNL protein
SEQ ID NO:8: PfalHNL gene
SEQ ID NO:9: Pton1HNL protein
SEQ ID NO:10: Pton1HNL gene
SEQ ID NO:11: PlamHNL protein
SEQ ID NO:12: PlamHNL gene
SEQ ID NO:13: RspHNL protein
SEQ ID NO:14 RspHNL gene
SEQ ID NO:15: Conserved amino acid sequence of millipede-derived HNL
SEQ ID NO:16: Conserved amino acid sequence of millipede-derived HNL
SEQ ID NO:17: Conserved amino acid sequence of millipede-derived HNL
SEQ ID NO:18: Conserved amino acid sequence of millipede-derived HNL
SEQ ID NO:19: Conserved amino acid sequence of millipede-derived HNL
SEQ ID NO:20: Conserved amino acid sequence of millipede-derived HNL
SEQ ID NO:21: Degenerate primer HNL-FW
SEQ ID NO:22: Degenerate primer HNL-RV
SEQ ID NO:23: Degenerate primer HNL-FW2
SEQ ID NO:24: Degenerate primer HNL-RV2
SEQ ID NOS:25 to 82: Primers
SEQ ID NO:83: PtokHNL protein
SEQ ID NO:84: PtokHNL gene
SEQ ID NO:85: Pton2HNL protein
SEQ ID NO:86: Pton2HNL gene
SEQ ID NO:87: Pton3HNL protein
SEQ ID NO:88: Pton3HNL gene
SEQ ID NO:89: RssHNL protein
SEQ ID NO:90: RssHNL gene
SEQ ID NOS:91 to 122: Primers
[Sequence Listing]

The invention claimed is:

1. A method for manufacturing a millipede-derived hydroxynitrile lyase (HNL) gene, comprising:

selecting a gene having at least one nucleotide sequence selected from a nucleotide sequence encoding the conserved amino acid sequence TAX$^1$DIX$^2$G (SEQ ID NO:15) (wherein X$^1$ is L or F, and X$^2$ is R or K) and a nucleotide sequence encoding the conserved amino acid sequence VPNGDKIH (SEQ ID NO:16) of millipede-derived HNL from the genes present in an organism belonging to a Diplopoda;

wherein the organism belonging to the Diplopoda is selected from the group consisting of *Nedyopus tambanus mangaesi-*

*nus, Oxidus gracilis, Parafontaria falcifera, Parafontaria laminata, Parafontaria tonominea* and *Riukiaria* sp.

2. The method according to claim 1, wherein selection of the gene is accomplished by performing PCR using a gene present in an organism belonging to the Diplopoda as a template, and using at least one DNA comprising a nucleotide sequence encoding for the conserved amino acid sequence as a primer.

3. The method according to claim 1, wherein selection of the gene is accomplished by performing DNA-DNA hybridization using a gene present in an organism belonging to the Diplopoda as a template, and using DNA comprising a nucleotide sequence encoding for the conserved amino acid sequence as a probe.

4. The method according to claim 1, wherein selection of the gene is accomplished by sequencing genes present in an organism belonging to the Diplopoda, and selecting a gene having a nucleotide sequence encoding for the conserved amino acid sequence from the sequenced gene sequences.

5. A method according to claim 1, wherein the gene present in an organism belonging to the Diplopoda is genome DNA extracted from an organism belonging to the Diplopoda, or cDNA obtained by reverse transcription of RNA extracted from an organism belonging to the Diplopoda.

6. The method according to claim 2, wherein the primers are the degenerate primers HNL-FW and HNL-RV or HNL-FW2 and HNL-RV2, said degenerate primers having the respective sequences:

```
HNL-FW:
                                 (SEQ ID NO: 21)
CTGCAACTGCATTGGAMATTCAAGG,

HNL-RV:
                                 (SEQ ID NO: 22)
ATGAATCTTRTCRCCGTTTGGAAC.

HNL-FW2:
                                 (SEQ ID NO: 23)
SSAACTGCATTGGAYATMMRAGG.
and HNL-RV2:
                                 (SEQ ID NO: 24)
ATGAATCTTRTCRCCRTTTGGRAC.
```

7. A method for manufacturing millipede-derived HNL, comprising:
preparing a millipede-derived HNL gene by a method according to claim 1, and causing the resulting HNL gene to be expressed in host cells to obtain the HNL.

8. The method according to claim 7, wherein the host cells are cultured insect cells.

9. The method according to claim 7, wherein the host cells are *E. coli* cells having disulfide bond isomerase expressing ability.

10. A gene having a nucleotide sequence having at least 90% sequence identity with the nucleotide sequence of any one of SEQ ID NOs: 2, 4, 6, 8, 10, 12, 14, 84, 86, 88 or 90 and containing at least one substitution modification relative to any one of SEQ ID NOs: 2, 4, 6, 8, 10, 12, 14, 84, 86, 88 or 90, and encoding for a protein having HNL activity.

11. A plasmid comprising the gene of claim 10 contained in a vector.

12. A transformant comprising a host containing a plasmid comprising the gene of claim 10 contained in a vector in such a way that the gene can be expressed, wherein the host is an insect cell or an *E. coli* having disulfide bond isomerase expressing ability.

13. A method for manufacturing a millipede-derived HNL, comprising culturing the transformant according to claim 12 and separating the HNL from the culture.

14. The method according to claim 13, wherein the host is cultured insect cells, and the HNL gene is an HNL gene derived from *Nedyopus tambanus mangaesinus, Oxidus gracilis, Parafontaria falcifera, Parafontaria laminata, Parafontaria tonominea* or *Riukiaria* sp.

15. The method according to claim 13, wherein the host is an *E. coli* having disulfide bond isomerase expressing ability, and the HNL gene is an HNL gene derived from *Nedyopus tambanus mangaesinus, Oxidus gracilis* or *Parafontaria laminata*.

16. A method for manufacturing an optically active cyanohydrin, comprising reacting a millipede-derived HNL with a reaction solution containing an aldehyde or ketone and hydrogen cyanide or a substance that produces cyanide ions in the reaction system to produce an optically active cyanohydrin, wherein the millipede-derived HNL is a protein having an amino acid sequence of any of (1) to (2) below, and having HNL activity:
(1) the amino acid sequence of any of SEQ ID NOS:1, 3, 5, 7, 9, 11, 13, 83, 85, 87 or 89 which is expressed by insect or bacterial cells;
(2) the amino acid sequence having at least 90% sequence identity with any of SEQ ID NOs:1, 3, 5, 7, 9, 11, 13, 83, 85, 87 or 89 and contains at least one amino acid substitution modification relative to any one of SEQ ID NOS: 1, 3, 5, 7, 9, 11, 13, 83, 85, 87 or 89.

17. A method for manufacturing an optically active cyanohydrin, comprising reacting a millipede-derived HNL with a reaction solution containing an aldehyde or ketone and hydrogen cyanide or a substance that produces cyanide ions in the reaction system to produce an optically active cyanohydrin, wherein the millipede-derived HNL is a transformant according to claim 12.

* * * * *

SEQUENCE LISTING

<160> NUMBER OF SEQ ID NOS: 122

<210> SEQ ID NO 1
<211> LENGTH: 182
<212> TYPE: PRT
<213> ORGANISM: Nedyopus tambanus tambanus

<400> SEQUENCE: 1

```
Met Leu Phe Tyr Val Ser Ile Leu Leu Val Val Thr Leu Thr Gly Ala
1               5                   10                  15

Glu Glu Glu Pro Leu Thr Cys Asp Lys Leu Pro Lys Val Pro Val Pro
            20                  25                  30

Pro Leu Glu Asp Phe Ile Asp Ser Asn Pro Leu Gln Phe Ala Tyr Val
        35                  40                  45

Leu Thr His Thr Phe Asp Cys Thr Thr Arg Val Tyr Val Arg Pro Gly
    50                  55                  60

Arg Leu Ser Pro Thr Gln Ala Ala Thr Ala Leu Asp Ile Gln Gly Ser
65                  70                  75                  80

His Val Ile Ala Asn Asp Phe Val Gly Gly Pro Asp Asn Ser Ala Ile
                85                  90                  95

Leu Thr Asn Cys Thr Thr Gly Glu Lys Thr Ile Trp His Phe Gln Tyr
            100                 105                 110

Thr Asn Leu Asn Thr Pro Asn Gly Ser Ser Tyr Cys Ala Tyr Thr Cys
        115                 120                 125

Asn Gly Ser Ala Ile Ala Glu Tyr Lys Cys Ala Asn Asn Asn Gly
    130                 135                 140

Thr Asp Pro Leu Gln Thr Gln Ala Val Glu Val Ala Lys Lys Val Pro
145                 150                 155                 160

Asn Gly Asp Lys Ile His Tyr Ala Leu Asp Asn Cys Pro Gln His His
                165                 170                 175

Gly Cys Phe Ala Phe Tyr
            180
```

<210> SEQ ID NO 2
<211> LENGTH: 549
<212> TYPE: DNA
<213> ORGANISM: Nedyopus tambanus tambanus

<400> SEQUENCE: 2

| | | | | | | |
|---|---|---|---|---|---|---|
| atgctgtttt | acgtttcgat | tcttctagtg | gtcacattaa | ctggagctga | ggaggaacca | 60 |
| ttgacatgcg | ataaacttcc | taaagttcca | gttcctccgt | tagaagattt | tattgattcg | 120 |
| aatcccttgc | aatttgctta | cgttctgacc | cacactttcg | attgtaccac | tagagtttac | 180 |
| gtgcgccctg | gtcgcttgtc | tcctacccag | gctgcaactg | cattggacat | tcaaggttca | 240 |
| catgttattg | ctaatgattt | cgttggtgga | cctgataact | ccgccatact | tactaattgt | 300 |
| actacaggcg | aaaaaactat | ctggcacttt | caatatacta | atttgaacac | cccaaatgga | 360 |
| agttcatatt | gcgcttatac | gtgcaatggt | tctgcaattg | cagagtataa | atgtgctaat | 420 |
| aataacaatg | gaaccgaccc | actccaaact | caagcagttg | aagttgctaa | gaaagttcca | 480 |
| aacggtgata | agattcatta | tgccttggac | aactgtccac | aacaccatgg | ttgttttgct | 540 |
| ttctattaa | | | | | | 549 |

<210> SEQ ID NO 3
<211> LENGTH: 182
<212> TYPE: PRT
<213> ORGANISM: Nedyopus tambanus mangaesinus

<400> SEQUENCE: 3

Met Leu Phe Tyr Val Ser Ile Leu Leu Val Val Ala Leu Ala Gly Ala
1               5                   10                  15

Glu Asp Glu Pro Leu Thr Cys Asp Lys Leu Pro Lys Val Pro Val Pro
            20                  25                  30

Pro Leu Gln Asp Phe Ile Asp Ser Asn Pro Leu Gln Phe Ala Tyr Val
        35                  40                  45

Leu Thr Asn Thr Phe Asp Cys Thr Thr Arg Val Tyr Val Arg Pro Gly
    50                  55                  60

Arg Leu Ser Pro Thr Gln Ala Ala Thr Ala Leu Asp Ile Gln Gly Ser
65                  70                  75                  80

His Val Ile Ala Asn Asp Phe Val Gly Gly Pro Asn Asn Ser Ala Ile
                85                  90                  95

Leu Thr Asn Cys Thr Thr Gly Glu Lys Thr Thr Trp Tyr Phe Gln Tyr
            100                 105                 110

Thr Asn Leu Asn Thr Pro Asp Gly Ser Ser Tyr Cys Ala Tyr Thr Cys
        115                 120                 125

Asn Gly Ala Ala Ile Ala Glu Tyr Lys Cys Ala Asn Asn Asn Asn Gly
    130                 135                 140

Thr Asp Pro Leu Gln Ile Gln Ala Val Glu Val Ala Lys Lys Val Pro
145                 150                 155                 160

Asn Gly Asp Lys Ile His Tyr Ala Leu Ala Asn Cys Pro Gln His His
                165                 170                 175

Gly Cys Phe Ala Phe Tyr
            180

<210> SEQ ID NO 4
<211> LENGTH: 549
<212> TYPE: DNA
<213> ORGANISM: Nedyopus tambanus mangaesinus

<400> SEQUENCE: 4
atgctgtttt acgtctcgat tcttctagtg gtcgcattag ctggagctga ggacgaacca      60
ttgacttgcg ataaacttcc caaagttcca gttcctccgt acaagagttt tattgattcg     120
aatcccttgc aatttgctta cgtcctgacc aacactttcg attgtaccac tagagtttac     180
gtgcgtcctg gtcgcttgtc tcctacccaa gccgcaactg cattggacat tcaaggttca     240
catgttattg ctaatgattt cgttggtgga cctaataact ccgccatact tactaattgc     300
actacaggcg aaaaaactac ctggtacttt caatatacta atctgaacac cccagatgga     360
agttcatatt gcgcttatac gtgcaatggc gctgcaattg cagagtataa atgtgctaat     420
aataacaatg gaaccgaccc actccaaatt caagcagttg aagttgctaa gaaagttcca     480
aacggtgata agattcatta tgccttggcc aactgtccac acaccatggg ctgttttgct     540
ttctattga                                                             549

<210> SEQ ID NO 5
<211> LENGTH: 184
<212> TYPE: PRT
<213> ORGANISM: Oxidus gracilis

<400> SEQUENCE: 5

Met Leu Tyr Tyr Val Ser Ile Leu Leu Met Ala Val Tyr Ala Val Ala
1               5                   10                  15

Val Ala Asp Glu Asp Pro Met Thr Cys Asp Lys Leu Pro Lys Val Pro
            20                  25                  30

Val Pro Pro Leu Glu Glu Phe Ile Lys Ser Asn Pro Leu Gln Phe Ala
                35                  40                  45

Tyr Val Leu Thr Asp Thr Phe Asp Cys Thr Arg Val Tyr Val Gln
 50                  55                  60

Pro Ala Arg Leu Ser Pro Asn Gln Ala Ala Thr Ala Leu Asp Ile Arg
 65                  70                  75                  80

Gly Ser Arg Ile Ile Thr Asn Asp Phe Val Gly Pro Asn Asn Ser
                 85                  90                  95

Ala Ile Leu Asn Asn Cys Thr Thr Gly Glu Lys Ala Thr Trp Tyr Phe
                100                 105                 110

Gln Tyr Thr Asn Leu Asn Thr Pro Asn Gly Ser Ser Tyr Cys Ala Tyr
            115                 120                 125

Thr Cys Asn Gly Glu Glu Ile Ala Glu Tyr Lys Cys Ala Asn Asn Asn
            130                 135                 140

Asn Gly Thr Asp Pro Leu Gln Lys Gln Ala Val Glu Val Ala Lys Lys
145                 150                 155                 160

Val Pro Asn Gly Asp Lys Ile His Tyr Ala Leu Asp Asn Cys Pro Glu
                165                 170                 175

His His Gly Cys Phe Ala Phe Tyr
                180

<210> SEQ ID NO 6
<211> LENGTH: 555
<212> TYPE: DNA
<213> ORGANISM: Oxidus gracilis

<400> SEQUENCE: 6
atgttgtact acgtttcaat acttttaatg gctgtctatg ctgtggctgt agcggatgaa      60
gacccaatga cttgcgataa acttcccaaa gttccagttc ctcctttaga ggaatttatt     120
aagtcaaatc ctttgcaatt tgcttacgtt ctgactgata cctttgattg taccactcga     180
gtttatgtgc agcctgctcg tttgtctccc aaccaagcgg caaccgcatt ggatattaga     240
ggttccagaa taattactaa tgatttcgtt ggtggtccta ataattcagc tattcttaat     300
aactgtacta caggagaaaa agcaacttgg tactttcaat acaccaatct gaacactcca     360
aatggaagct cctattgcgc ctacacgtgc aatggagaag aaattgcaga atataaatgc     420
gctaataaca acaacggaac cgatccactt caaaaacaag cggtagaagt tgctaaaaaa     480
gttccaaacg gtgataagat tcattatgcc ctggacaact gtcctgaaca ccatggctgt     540 tttgcttttct attag                                                    555

<210> SEQ ID NO 7
<211> LENGTH: 189
<212> TYPE: PRT
<213> ORGANISM: Parafontaria falcifera

<400> SEQUENCE: 7

Met Thr Ser Ile Ile Phe Leu Thr Thr Val Ala Leu Ile Val Met Leu
  1               5                  10                  15

Ala Glu Leu Gly Trp Ala Gln Pro Ser Gly Leu Thr Cys Asp Gln Leu
                20                  25                  30

Asp Lys Val Val Pro Pro Gly Ile Ser Ala Phe Ile Ser Asn Asn Pro
             35                  40                  45

Phe Glu Phe Ser Tyr Val Leu Thr Lys Thr Phe Asp Cys Thr Ala Arg
 50                  55                  60

Val Tyr Val Gln Pro Val His Gly Leu Thr Asn Tyr Ser Gly Thr Ala
 65                  70                  75                  80

Leu Asp Ile Arg Gly Thr His Ile Ile Ile Asn Asp Phe Thr Ile Gly
                 85                  90                  95

Ser Asp Ser Met Thr Ala Phe Leu Thr Asn Cys Asp Asn Gly Lys Lys
            100                 105                 110

Gln Val Trp His Phe Gln Tyr Ile Asp Leu Asn Asp Pro Gln Gly Ala
        115                 120                 125

Asn Tyr Cys Ala Tyr Ser Cys Asn Gly Pro Glu Ile Val Glu Tyr Lys
    130                 135                 140

Cys Thr Thr Asn Thr Gly Tyr Ile Ser Ala Thr Gln Arg Gln Ala Val
145                 150                 155                 160

Lys Lys Ala Gln Leu Val Pro Asn Gly Tyr Lys Ile His Leu Ala Gln
                165                 170                 175

Asp Asn Cys Pro Pro His Pro Phe Cys Pro Leu Tyr Tyr
            180                 185

<210> SEQ ID NO 8
<211> LENGTH: 570
<212> TYPE: DNA
<213> ORGANISM: Parafontaria falcifera

<400> SEQUENCE: 8
atgacttcga tcattttcct cacgactgta gcactgatcg ttatgttggc cgaattgggc      60
tgggctcaac cttcaggtct cacttgcgac caactcgaca aagtcgtccc acctggcatt     120
agtgctttca tttccaacaa tccttttgaa ttctcgtatg tgttgactaa aactttcgac     180
tgtaccgcac gagtctacgt acagcctgta catggactga ccaattacag tggaactgca     240
ctggacatca gaggaactca cataataatt aatgacttca ccattggttc tgattctatg     300 acagccttt tgactaattg cgataatgga aaaaaacagg tttggcattt tcaatatatc      360
gacctaaatg atccccaagg tgccaactat tgtgcatact cttgcaatgg tcccgaaata     420
gtcgaataca aatgcactac gaatactgga tacatatcag ctacacaacg tcaggctgta     480
aaaaaggcac aattagttcc aaacggctat aagatccatc tagcccagga caattgccct     540 cctcacccttt ctgtcctct ctattactaa                                      570

<210> SEQ ID NO 9
<211> LENGTH: 189
<212> TYPE: PRT
<213> ORGANISM: Parafontaria tonominea

<400> SEQUENCE: 9

Met Thr Ser Ile Ile Leu Leu Leu Ala Ala Ala Leu Thr Val Met Leu
 1               5                  10                  15

Ala Glu Leu Gly Trp Ala Gln Pro Ser Gly Leu Ala Cys Asp Gln Leu
                20                  25                  30

Pro Lys Val Ser Pro Pro Gly Ile Ser Ala Phe Ile Ser His Asn Pro
            35                  40                  45

Phe Glu Phe Thr Tyr Val Leu Thr Asp Thr Phe Asp Cys Thr Ala Arg
        50                  55                  60

Val Tyr Val Gln Pro Val His Gly Leu Thr Asn Tyr Ser Gly Thr Ala
 65                  70                  75                  80

Leu Asp Ile Arg Gly Thr His Ile Ile Ile Asn Asp Phe Thr Ile Gly
                 85                  90                  95

Pro Asp Ala Met Thr Ala Tyr Leu Thr Asn Cys Asp Asn Asp Glu Lys
            100                 105                 110

Gln Val Trp His Phe Gln Tyr Val Asp Leu Asp Asp Pro Gln Gly Ala
        115                 120                 125

Asn Tyr Cys Ala Tyr Phe Cys Asn Gly Pro Asn Ile Val Glu Tyr Lys
    130                 135                 140

Cys Thr Thr Asn Thr Gly Tyr Ile Ser Pro Gln Gln Leu Gln Ala Val
145                 150                 155                 160

Lys Glu Ala Gln Ser Val Pro Asn Gly Asp Lys Ile His Leu Ala Gln
                165                 170                 175

Ala Asn Cys Pro Pro His Pro Phe Cys Pro Leu Tyr Tyr
                180                 185

<210> SEQ ID NO 10
<211> LENGTH: 570
<212> TYPE: DNA
<213> ORGANISM: Parafontaria tonominea

<400> SEQUENCE: 10
atgacttcaa tcattctcct cttggctgca gcactgaccg ttatgttggc cgaattgggc      60
tgggctcaac cttcaggtct cgcttgcgac cagctcccca agtcagccca ccaggcatt     120 agtgctttca tttcccataa tccttttgaa ttcacgtatg ttttgactga cactttcgac     180
tgtaccgcac gagtctacgt acagcctgta catggactga ccaattacag tggaactgca     240
ctggacatca gaggaactca catcataatt aatgacttca ccattggtcc cgatgctatg     300
acggcctatt tgactaattg cgataatgac gaaaaacagg tttggcattt tcaatatgtc     360
gacctagatg atccccaagg tgccaactat tgtgcatact tttgcaatgg tcccaacata     420
gtggaataca aatgcactac gaatactgga tacatatcgc ctcaacaact ccaggctgta     480
aaagaggcac aatcagtccc aaatggtgac aagatccatc tagcccaggc caattgccct     540 cctcacccttt ctgtcctct ctattactaa                                       570

<210> SEQ ID NO 11
<211> LENGTH: 190
<212> TYPE: PRT
<213> ORGANISM: Parafontaria laminata

<400> SEQUENCE: 11

Met Thr Ser Ile Ile Leu Leu Met Thr Val Ala Ala Leu Ile Val Met
1               5                   10                  15

Leu Ala Glu Leu Gly Trp Ala Gln Pro Ser Pro Leu Thr Cys Asp Lys
            20                  25                  30

Leu Pro Lys Val Ile Pro Pro Gly Ile Ser Ala Phe Thr Ser His Asn
        35                  40                  45

Pro Phe Glu Phe Ser Tyr Val Leu Thr Asn Asp Leu Asp Cys Thr Ala
    50                  55                  60

Arg Val Tyr Val Gln Pro Val His Gly Leu Thr Asn Tyr Ser Gly Thr
65                  70                  75                  80

Ala Phe Asp Ile Lys Gly Thr His Ile Thr Ile Asn Asp Phe Thr Ile
                85                  90                  95

Gly Ala Asp Gly Leu Thr Ala Tyr Leu Thr Asn Cys Asp Thr Asp Val
            100                 105                 110

Lys Gln Val Trp His Phe Gln Tyr Val Asp Leu Gly Asp Pro Gln Gly
        115                 120                 125

```
Ala Asn Tyr Cys Ala Tyr Tyr Cys Glu Gly Pro Glu Ile Val Glu Tyr
        130                 135                 140

Lys Cys Thr Thr Asn Thr Gly Tyr Ile Ser Pro Arg Gln Leu Gln Ala
145                 150                 155                 160

Val Lys Glu Ala Gln Ser Val Pro Asn Gly Asp Lys Ile His Pro Ala
                165                 170                 175

Gln Val Asn Cys Pro Pro His Leu Tyr Cys Pro Leu Tyr Tyr
            180                 185                 190

<210> SEQ ID NO 12
<211> LENGTH: 573
<212> TYPE: DNA
<213> ORGANISM: Parafontaria laminata

<400> SEQUENCE: 12
atgacttcga tcattctcct catgactgtt gctgcactga tcgttatgtt ggccgaattg      60
ggctgggctc aaccttcacc tctcacttgc gacaagctcc caaaagtcat cccacctggc     120
attagtgctt tcacttccca caatccttt gaattctcgt atgtgttgac taacgatctc      180
gactgtaccg cacgagtcta cgtacagcct gtacatggac tgaccaatta cagtggaact     240
gcatttgaca tcaaaggaac tcacataaca ataaatgact tcaccattgg tgccgatggt     300
ctgacagcct atttgactaa ttgtgatact gacgtaaaac aggtttggca ttttcaatat     360
gtcgacctag tgatcccca aggtgccaac tattgtgcat actattgcga aggtcccgaa      420
atagtggaat acaaatgcac tacgaatact ggatacatat cgcctcgaca actccaggct     480
gtaaaagagg cacaatcagt cccaaatggt gacaagattc atccagccca ggtcaattgc     540
cctcctcacc tttactgtcc cctctattac taa                                  573

<210> SEQ ID NO 13
<211> LENGTH: 188
<212> TYPE: PRT
<213> ORGANISM: Riukiaria sp.

<400> SEQUENCE: 13

Met Thr Ser Ile Met Phe Ser Leu Thr Leu Ala Leu Thr Ala Met Met
1               5                   10                  15

Ala Glu Leu Gly Trp Ala Gln Pro Pro Asp Gly Pro Ser Cys Glu Asn
                20                  25                  30

Leu Pro Lys Val Cys Pro Pro Gly Leu Asp Ala Phe Ile Ser His Asn
            35                  40                  45

Pro Phe Leu Phe Glu Phe Val Leu Ser Asp Ser Leu Asp Cys Thr Thr
        50                  55                  60

Arg Val Tyr Val Gln Pro Ala Arg Gly Tyr Thr Asn Tyr Ser Gly Thr
65                  70                  75                  80

Ala Phe Asp Ile Arg Lys Asn His Ile Asp Ile Asn Asp Phe Leu Ile
                85                  90                  95

Ala Ala Asp Cys Ile Ala Tyr Leu Thr Asn Cys Asp Thr Gly Ala Lys
            100                 105                 110

Gln Val Trp Tyr Phe Gln Tyr Val Asp Leu Asp Pro Leu Gly Ala
        115                 120                 125

Asn Tyr Cys Ala Tyr Ser Cys Asn Gly Ala Ser Ile Val Glu Tyr Lys
    130                 135                 140

Cys Thr Ser Asn Thr Gly Tyr Ile Ser Gln Lys Gln Lys Asp Ala Val
145                 150                 155                 160
```

Ala Glu Ala Lys Lys Val Pro Asn Gly Asp Lys Ile His Pro Gly Gln
                165                 170                 175

Ile Gly Cys Ala Tyr Pro Ile Cys Pro Phe Tyr Ser
            180                 185

<210> SEQ ID NO 14
<211> LENGTH: 567
<212> TYPE: DNA
<213> ORGANISM: Riukiaria sp.

<400> SEQUENCE: 14
atgacttcga tcatgttcag cctgacttta gcactgactg ctatgatggc cgaattgggc     60
tgggctcaac ctcctgacgg cccttcctgc gaaaatctcc ccaaagtctg cccaccaggt    120
ctcgatgctt tcatttccca caatccgttt ttattcgagt tgtgttgag cgacagtttg     180 gactgcacca cacgagtcta cgtgcagcct gcacgtggat acaccaatta cagtggcacc    240
gcatttgaca taagaaaaaa tcatatagac attaatgact tcctcatcgc tgctgattgt    300
atcgcctatt tgaccaattg tgataccggg caaaacagg tttggtattt tcaatatgtc     360
gacctcgatg atcccctggg tgccaactat tgcgcatact cttgcaatgg tgcctctata    420
gtggaataca atgcacttc caatactggc tatatatcgc aaaagcaaaa ggatgcagtg     480
gcagaggcta aaaagtccc aaatggtgac aagatccacc caggccagat cggctgcgct     540
taccctatct gccccttcta tagctaa                                        567

<210> SEQ ID NO 15
<211> LENGTH: 7
<212> TYPE: PRT
<213> ORGANISM: Artificial sequence
<220> FEATURE:
<223> OTHER INFORMATION: Common sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 15

Thr Ala Xaa Asp Ile Xaa Gly
1               5

<210> SEQ ID NO 16
<211> LENGTH: 8
<212> TYPE: PRT
<213> ORGANISM: Artificial sequence
<220> FEATURE:
<223> OTHER INFORMATION: Common sequence

<400> SEQUENCE: 16

Val Pro Asn Gly Asp Lys Ile His
1               5

<210> SEQ ID NO 17
<211> LENGTH: 7
<212> TYPE: PRT
<213> ORGANISM: Artificial sequence
<220> FEATURE:
<223> OTHER INFORMATION: Common sequence

```
<400> SEQUENCE: 17

Thr Ala Leu Asp Ile Arg Gly
1               5

<210> SEQ ID NO 18
<211> LENGTH: 7
<212> TYPE: PRT
<213> ORGANISM: Artificial sequence
<220> FEATURE:
<223> OTHER INFORMATION: Common sequence

<400> SEQUENCE: 18

Thr Ala Leu Asp Ile Lys Gly
1               5

<210> SEQ ID NO 19
<211> LENGTH: 7
<212> TYPE: PRT
<213> ORGANISM: Artificial sequence
<220> FEATURE:
<223> OTHER INFORMATION: Common sequence

<400> SEQUENCE: 19

Thr Ala Phe Asp Ile Arg Gly
1               5

<210> SEQ ID NO 20
<211> LENGTH: 7
<212> TYPE: PRT
<213> ORGANISM: Artificial sequence
<220> FEATURE:
<223> OTHER INFORMATION: Common sequence

<400> SEQUENCE: 20

Thr Ala Phe Asp Ile Lys Gly
1               5

<210> SEQ ID NO 21
<211> LENGTH: 25
<212> TYPE: DNA
<213> ORGANISM: Artificial sequence
<220> FEATURE:
<223> OTHER INFORMATION: Primer

<400> SEQUENCE: 21
ctgcaactgc attggamatt caagg                                         25

<210> SEQ ID NO 22
<211> LENGTH: 24
<212> TYPE: DNA
<213> ORGANISM: Artificial sequence
<220> FEATURE:
<223> OTHER INFORMATION: Primer

<400> SEQUENCE: 22
atgaatcttr tcrccgtttg gaac                                          24

<210> SEQ ID NO 23
<211> LENGTH: 23
<212> TYPE: DNA
<213> ORGANISM: Artificial sequence
<220> FEATURE:
<223> OTHER INFORMATION: Primer

<400> SEQUENCE: 23
ssaactgcat tggayatmmr agg                                           23
```

```
<210> SEQ ID NO 24
<211> LENGTH: 24
<212> TYPE: DNA
<213> ORGANISM: Artificial sequence
<220> FEATURE:
<223> OTHER INFORMATION: Primer

<400> SEQUENCE: 24
atgaatcttr tcrccrtttg grac                                            24

<210> SEQ ID NO 25
<211> LENGTH: 23
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 25
gargarccnh tnacntgyga taa                                             23

<210> SEQ ID NO 26
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 26
ttytcnacng cytgngtctg                                                 20

<210> SEQ ID NO 27
<211> LENGTH: 27
<212> TYPE: DNA
<213> ORGANISM: Artificial sequence
<220> FEATURE:
<223> OTHER INFORMATION: Primer

<400> SEQUENCE: 27
gttccagttc ctccgttaga agatttt                                         27

<210> SEQ ID NO 28
<211> LENGTH: 26
<212> TYPE: DNA
<213> ORGANISM: Artificial sequence
<220> FEATURE:
<223> OTHER INFORMATION: Primer
```

```
<400> SEQUENCE: 28
cccaggctgc aactgcattg gacatt                                          26

<210> SEQ ID NO 29
<211> LENGTH: 28
<212> TYPE: DNA
<213> ORGANISM: Artificial sequence
<220> FEATURE:
<223> OTHER INFORMATION: Primer

<400> SEQUENCE: 29
ctctgcaatt gcagaaccat tgcacgta                                        28

<210> SEQ ID NO 30
<211> LENGTH: 28
<212> TYPE: DNA
<213> ORGANISM: Artificial sequence
<220> FEATURE:
<223> OTHER INFORMATION: Primer

<400> SEQUENCE: 30
ccatttgggg tgttcaaatt agtatatt                                        28

<210> SEQ ID NO 31
<211> LENGTH: 28
<212> TYPE: DNA
<213> ORGANISM: Artificial sequence
<220> FEATURE:
<223> OTHER INFORMATION: Primer

<400> SEQUENCE: 31
atgctgtttt acgtttcgat tcttctag                                        28

<210> SEQ ID NO 32
<211> LENGTH: 27
<212> TYPE: DNA
<213> ORGANISM: Artificial sequence
<220> FEATURE:
<223> OTHER INFORMATION: Primer

<400> SEQUENCE: 32
ttaatagaaa gcaaacaac catggtg                                          27

<210> SEQ ID NO 33
<211> LENGTH: 25
<212> TYPE: DNA
<213> ORGANISM: Artificial sequence
<220> FEATURE:
<223> OTHER INFORMATION: Primer

<400> SEQUENCE: 33
tggtggacct aataactccg ccata                                           25

<210> SEQ ID NO 34
<211> LENGTH: 27
<212> TYPE: DNA
<213> ORGANISM: Artificial sequence
<220> FEATURE:
<223> OTHER INFORMATION: Primer

<400> SEQUENCE: 34
cccagatgga agttcatatt gcgctta                                         27
```

<210> SEQ ID NO 35
<211> LENGTH: 26
<212> TYPE: DNA
<213> ORGANISM: Artificial sequence
<220> FEATURE:
<223> OTHER INFORMATION: Primer

<400> SEQUENCE: 35
gagtgggtcg gttccattgt tattat                                   26

<210> SEQ ID NO 36
<211> LENGTH: 25
<212> TYPE: DNA
<213> ORGANISM: Artificial sequence
<220> FEATURE:
<223> OTHER INFORMATION: Primer

<400> SEQUENCE: 36
gccattgcac gtataagcgc aatat                                    25

<210> SEQ ID NO 37
<211> LENGTH: 27
<212> TYPE: DNA
<213> ORGANISM: Artificial sequence
<220> FEATURE:
<223> OTHER INFORMATION: Primer

<400> SEQUENCE: 37
cgttggtggt cctaataatt cagctat                                  27

<210> SEQ ID NO 38
<211> LENGTH: 26
<212> TYPE: DNA
<213> ORGANISM: Artificial sequence
<220> FEATURE:
<223> OTHER INFORMATION: Primer

<400> SEQUENCE: 38
caccaatctg aacactccaa atggaa                                   26

<210> SEQ ID NO 39
<211> LENGTH: 24
<212> TYPE: DNA
<213> ORGANISM: Artificial sequence
<220> FEATURE:
<223> OTHER INFORMATION: Primer

<400> SEQUENCE: 39
ggatcggttc cgttgttgtt atta                                     24

<210> SEQ ID NO 40
<211> LENGTH: 27
<212> TYPE: DNA
<213> ORGANISM: Artificial sequence
<220> FEATURE:
<223> OTHER INFORMATION: Primer

<400> SEQUENCE: 40
cgtataggcg caataggagc ttccatt                                  27

<210> SEQ ID NO 41
<211> LENGTH: 26
<212> TYPE: DNA
<213> ORGANISM: Artificial sequence
<220> FEATURE:
<223> OTHER INFORMATION: Primer

<400> SEQUENCE: 41
gacttcacca ttggttctga ttctat                                    26

<210> SEQ ID NO 42
<211> LENGTH: 26
<212> TYPE: DNA
<213> ORGANISM: Artificial sequence
<220> FEATURE:
<223> OTHER INFORMATION: Primer

<400> SEQUENCE: 42
ccccaaggtg ccaactattg tgcata                                    26

<210> SEQ ID NO 43
<211> LENGTH: 27
<212> TYPE: DNA
<213> ORGANISM: Artificial sequence
<220> FEATURE:
<223> OTHER INFORMATION: Primer

<400> SEQUENCE: 43
cagcctgacg ttgtgtagct gatatgt                                   27

<210> SEQ ID NO 44
<211> LENGTH: 27
<212> TYPE: DNA
<213> ORGANISM: Artificial sequence
<220> FEATURE:
<223> OTHER INFORMATION: Primer

<400> SEQUENCE: 44
cgggaccatt gcaagagtat gcacaat                                   27

<210> SEQ ID NO 45
<211> LENGTH: 33
<212> TYPE: DNA
<213> ORGANISM: Artificial sequence
<220> FEATURE:
<223> OTHER INFORMATION: Primer

<400> SEQUENCE: 45
attcaaggaa ctcacataac aataaatgac ttc                            33

<210> SEQ ID NO 46
<211> LENGTH: 30
<212> TYPE: DNA
<213> ORGANISM: Artificial sequence
<220> FEATURE:
<223> OTHER INFORMATION: Primer

<400> SEQUENCE: 46
atgaatcttg tcaccgtttg gaactgatcg                                30

<210> SEQ ID NO 47
<211> LENGTH: 31
<212> TYPE: DNA
<213> ORGANISM: Artificial sequence
<220> FEATURE:
<223> OTHER INFORMATION: Primer

<400> SEQUENCE: 47
gagttgttta ggcgatatgt atccagtatt c                              31

-continued

```
<210> SEQ ID NO 48
<211> LENGTH: 31
<212> TYPE: DNA
<213> ORGANISM: Artificial sequence
<220> FEATURE:
<223> OTHER INFORMATION: Primer

<400> SEQUENCE: 48
gagttgttta ggcgatatgt atccagtatt c                                31

<210> SEQ ID NO 49
<211> LENGTH: 25
<212> TYPE: DNA
<213> ORGANISM: Artificial sequence
<220> FEATURE:
<223> OTHER INFORMATION: Primer

<400> SEQUENCE: 49
ggtcccgatg ctatgacggc ctatt                                       25

<210> SEQ ID NO 50
<211> LENGTH: 25
<212> TYPE: DNA
<213> ORGANISM: Artificial sequence
<220> FEATURE:
<223> OTHER INFORMATION: Primer

<400> SEQUENCE: 50
ggtgccaact attgtgcata cttt                                        25

<210> SEQ ID NO 51
<211> LENGTH: 26
<212> TYPE: DNA
<213> ORGANISM: Artificial sequence
<220> FEATURE:
<223> OTHER INFORMATION: Primer

<400> SEQUENCE: 51
gcctggagtt gttgaggcga tatgta                                      26

<210> SEQ ID NO 52
<211> LENGTH: 27
<212> TYPE: DNA
<213> ORGANISM: Artificial sequence
<220> FEATURE:
<223> OTHER INFORMATION: Primer

<400> SEQUENCE: 52
gggaccattg caaaagtatg cacaata                                     27

<210> SEQ ID NO 53
<211> LENGTH: 22
<212> TYPE: DNA
<213> ORGANISM: Artificial sequence
<220> FEATURE:
<223> OTHER INFORMATION: Primer

<400> SEQUENCE: 53
ccggggcaaa acaggtttgg ta                                          22

<210> SEQ ID NO 54
<211> LENGTH: 26
<212> TYPE: DNA
<213> ORGANISM: Artificial sequence
<220> FEATURE:
<223> OTHER INFORMATION: Primer
```

<400> SEQUENCE: 54
gggtgccaac tattgcgcat actctt                                          26

<210> SEQ ID NO 55
<211> LENGTH: 26
<212> TYPE: DNA
<213> ORGANISM: Artificial sequence
<220> FEATURE:
<223> OTHER INFORMATION: Primer

<400> SEQUENCE: 55
gccagtattg gaagtgcatt tgtatt                                          26

<210> SEQ ID NO 56
<211> LENGTH: 26
<212> TYPE: DNA
<213> ORGANISM: Artificial sequence
<220> FEATURE:
<223> OTHER INFORMATION: Primer

<400> SEQUENCE: 56 cagggatca tcgaggtcga catatt                                           26

<210> SEQ ID NO 57
<211> LENGTH: 25
<212> TYPE: DNA
<213> ORGANISM: Artificial sequence
<220> FEATURE:
<223> OTHER INFORMATION: Primer

<400> SEQUENCE: 57
atgctgtttt acgtctcgat tcttc                                           25

<210> SEQ ID NO 58
<211> LENGTH: 25
<212> TYPE: DNA
<213> ORGANISM: Artificial sequence
<220> FEATURE:
<223> OTHER INFORMATION: Primer

<400> SEQUENCE: 58
tcaatagaaa gcaaacagc catgg                                            25

<210> SEQ ID NO 59
<211> LENGTH: 25
<212> TYPE: DNA
<213> ORGANISM: Artificial sequence
<220> FEATURE:
<223> OTHER INFORMATION: Primer

<400> SEQUENCE: 59
atgttgtact acgtttcaat acttt                                           25

<210> SEQ ID NO 60
<211> LENGTH: 25
<212> TYPE: DNA
<213> ORGANISM: Artificial sequence
<220> FEATURE:
<223> OTHER INFORMATION: Primer

<400> SEQUENCE: 60
ctaatagaaa gcaaacagc catgg                                            25

```
<210> SEQ ID NO 61
<211> LENGTH: 24
<212> TYPE: DNA
<213> ORGANISM: Artificial sequence
<220> FEATURE:
<223> OTHER INFORMATION: Primer

<400> SEQUENCE: 61
atgacttcga tcattttcct cacg                                            24

<210> SEQ ID NO 62
<211> LENGTH: 25
<212> TYPE: DNA
<213> ORGANISM: Artificial sequence
<220> FEATURE:
<223> OTHER INFORMATION: Primer

<400> SEQUENCE: 62
ttagtaatag agaggacaga aaggg                                           25

<210> SEQ ID NO 63
<211> LENGTH: 28
<212> TYPE: DNA
<213> ORGANISM: Artificial sequence
<220> FEATURE:
<223> OTHER INFORMATION: Primer

<400> SEQUENCE: 63
atgacttcga tcattctcct catgactg                                        28

<210> SEQ ID NO 64
<211> LENGTH: 32
<212> TYPE: DNA
<213> ORGANISM: Artificial sequence
<220> FEATURE:
<223> OTHER INFORMATION: Primer

<400> SEQUENCE: 64
gcttaattca attgcacttt aatttttata tc                                   32

<210> SEQ ID NO 65
<211> LENGTH: 25
<212> TYPE: DNA
<213> ORGANISM: Artificial sequence
<220> FEATURE:
<223> OTHER INFORMATION: Primer

<400> SEQUENCE: 65
atgacttcaa tcattctcct cttgg                                           25

<210> SEQ ID NO 66
<211> LENGTH: 27
<212> TYPE: DNA
<213> ORGANISM: Artificial sequence
<220> FEATURE:
<223> OTHER INFORMATION: Primer

<400> SEQUENCE: 66
ttagtaatag agaggacaga aagggtg                                         27

<210> SEQ ID NO 67
<211> LENGTH: 24
<212> TYPE: DNA
<213> ORGANISM: Artificial sequence
<220> FEATURE:
<223> OTHER INFORMATION: Primer
```

<400> SEQUENCE: 67
atgacttcga tcatgttcag cctg                                              24

<210> SEQ ID NO 68
<211> LENGTH: 25
<212> TYPE: DNA
<213> ORGANISM: Artificial sequence
<220> FEATURE:
<223> OTHER INFORMATION: Primer

<400> SEQUENCE: 68
ttagctatag aaggggcaga taggg                                             25

<210> SEQ ID NO 69
<211> LENGTH: 34
<212> TYPE: DNA
<213> ORGANISM: Artificial sequence
<220> FEATURE:
<223> OTHER INFORMATION: Primer

<400> SEQUENCE: 69
ggatccatgt tgagttcact agtagtaaca gtaa                                   34

<210> SEQ ID NO 70
<211> LENGTH: 35
<212> TYPE: DNA
<213> ORGANISM: Artificial sequence
<220> FEATURE:
<223> OTHER INFORMATION: Primer

<400> SEQUENCE: 70
aagcttagta aaaagcaaag caaccgtggg tttcg                                  35

<210> SEQ ID NO 71
<211> LENGTH: 34
<212> TYPE: DNA
<213> ORGANISM: Artificial sequence
<220> FEATURE:
<223> OTHER INFORMATION: Primer

<400> SEQUENCE: 71
gggcgcggat ccatgctgtt ttacgtttcg attc                                   34

<210> SEQ ID NO 72
<211> LENGTH: 41
<212> TYPE: DNA
<213> ORGANISM: Artificial sequence
<220> FEATURE:
<223> OTHER INFORMATION: Primer

<400> SEQUENCE: 72
acttctcgac aagcttttaa tagaaagcaa aacaaccatg g                           41

<210> SEQ ID NO 73
<211> LENGTH: 41
<212> TYPE: DNA
<213> ORGANISM: Artificial sequence
<220> FEATURE:
<223> OTHER INFORMATION: Primer

<400> SEQUENCE: 73
catcgggcgc ggatccatgc tgttttacgt ttcgattctt c                           41

```
<210> SEQ ID NO 74
<211> LENGTH: 41
<212> TYPE: DNA
<213> ORGANISM: Artificial sequence
<220> FEATURE:
<223> OTHER INFORMATION: Primer

<400> SEQUENCE: 74
acttctcgac aagctttcaa tagaaagcaa aacagccatg g                    41

<210> SEQ ID NO 75
<211> LENGTH: 38
<212> TYPE: DNA
<213> ORGANISM: Artificial sequence
<220> FEATURE:
<223> OTHER INFORMATION: Primer

<400> SEQUENCE: 75
catcgggcgc ggatccatgt tgtactacgt ttcaatac                        38

<210> SEQ ID NO 76
<211> LENGTH: 40
<212> TYPE: DNA
<213> ORGANISM: Artificial sequence
<220> FEATURE:
<223> OTHER INFORMATION: Primer

<400> SEQUENCE: 76
acttctcgac aagcttctaa tagaaagcaa aacagccatg                      40

<210> SEQ ID NO 77
<211> LENGTH: 40
<212> TYPE: DNA
<213> ORGANISM: Artificial sequence
<220> FEATURE:
<223> OTHER INFORMATION: Primer

<400> SEQUENCE: 77
catcgggcgc ggatccatga cttcgatcat tttcctcacg                      40

<210> SEQ ID NO 78
<211> LENGTH: 41
<212> TYPE: DNA
<213> ORGANISM: Artificial sequence
<220> FEATURE:
<223> OTHER INFORMATION: Primer

<400> SEQUENCE: 78
acttctcgac aagcttttag taatagagag gacagaaagg g                    41

<210> SEQ ID NO 79
<211> LENGTH: 40
<212> TYPE: DNA
<213> ORGANISM: Artificial sequence
<220> FEATURE:
<223> OTHER INFORMATION: Primer

<400> SEQUENCE: 79
catcgggcgc ggatccatga cttcaatcat tctcctcttg                      40

<210> SEQ ID NO 80
<211> LENGTH: 43
<212> TYPE: DNA
<213> ORGANISM: Artificial sequence
<220> FEATURE:
<223> OTHER INFORMATION: Primer
```

<400> SEQUENCE: 80
acttctcgac aagctttag taatagagag gacagaaagg gtg                43

<210> SEQ ID NO 81
<211> LENGTH: 40
<212> TYPE: DNA
<213> ORGANISM: Artificial sequence
<220> FEATURE:
<223> OTHER INFORMATION: Primer

<400> SEQUENCE: 81
catcgggcgc ggatccatga cttcgatcat gttcagcctg                40

<210> SEQ ID NO 82
<211> LENGTH: 41
<212> TYPE: DNA
<213> ORGANISM: Artificial sequence
<220> FEATURE:
<223> OTHER INFORMATION: Primer

<400> SEQUENCE: 82
acttctcgac aagctttag ctatagaagg ggcagatagg g                41

<210> SEQ ID NO 83
<211> LENGTH: 188
<212> TYPE: PRT
<213> ORGANISM: Parafontaria tokaiensis

<400> SEQUENCE: 83

Met Thr Ser Ile Ile Leu Leu Thr Thr Val Ala Leu Ser Val Met Leu
1               5                   10                  15

Ala Glu Leu Gly Trp Ala Val Ser Ala Leu Thr Cys Asp His Leu Pro
            20                  25                  30

Lys Val Ile Pro Pro Gly Ile Ser Ala Phe Ala Ser Asn Asn Pro Phe
        35                  40                  45

Glu Phe Ser Tyr Val Leu Thr Asn Asp Ile Asp Cys Thr Ala Arg Val
    50                  55                  60

Tyr Val Gln Pro Val His Gly Leu Thr Asn Tyr Ser Gly Thr Ala Phe
65                  70                  75                  80

Asp Ile Arg Gly Thr His Ile Thr Ile Asn Asp Phe Thr Ile Ala Pro
                85                  90                  95

Asp Gly Leu Thr Ala Tyr Leu Thr Asn Cys Asp Thr Asp Glu Lys Gln
            100                 105                 110

Val Trp Asn Phe Gln Tyr Val Asp Leu Asp Asp Pro Gln Gly Ala Asn
        115                 120                 125

Tyr Cys Ala Tyr Ser Cys Asn Gly Pro Glu Ile Val Glu Tyr Lys Cys
    130                 135                 140

Thr Thr Asn Thr Gly Tyr Ile Ser Ala Gln Gln Leu Gln Ala Val Lys
145                 150                 155                 160

Glu Ala Gln Ser Val Pro Asn Gly Asp Lys Ile His Leu Ala Gln Val
                165                 170                 175

Asn Cys Pro Pro His Leu Phe Cys Pro Leu Tyr Tyr
            180                 185

<210> SEQ ID NO 84
<211> LENGTH: 567
<212> TYPE: DNA
<213> ORGANISM: Parafontaria tokaiensis

<400> SEQUENCE: 84

```
atgacttcga tcattctcct cacgactgta gcactgagcg ttatgttggc cgaattgggc    60
tgggctgtgt cagcattgac ttgcgaccat ctccccaaag tcatcccacc tggcattagt   120
gctttcgctt ccaacaatcc ttttgaattc tcgtatgtgt tgactaacga tatcgattgt   180
accgcacgag tctatgtaca gcctgtacat ggactgacca attacagtgg aactgcattt   240
gacatcagag gaactcacat aacaataaat gacttcacca ttgctcccga tggtctgaca   300
gcctatttga ctaattgtga tactgacgaa aaacaggttt ggaattttca atatgtcgac   360
ctagatgatc cccaaggtgc caactattgt gcatactctt gcaatggtcc cgaaatagtg   420
gaatacaaat gcactacaaa tactggatac atatcggctc aacaactcca agctgtaaaa   480
gaggcacaat cagtcccgaa tggtgacaag atccatctag ctcaggtcaa ttgccctcct   540
cacctttcct gtcccctcta ttactaa                                       567
```

<210> SEQ ID NO 85
<211> LENGTH: 188
<212> TYPE: PRT
<213> ORGANISM: Parafontaria tonominea

<400> SEQUENCE: 85

```
Met Thr Ser Ile Ile Leu Leu Thr Thr Val Ala Leu Ile Val Met Leu
1               5                   10                  15
Ala Glu Leu Gly Trp Ala Val Ser Gly Leu Thr Cys Asp Gln Leu Pro
            20                  25                  30
Asn Val Ile Pro Pro Gly Ile Ser Ala Phe Ala Ser Asn Asn Pro Phe
        35                  40                  45
Glu Phe Ser Tyr Val Leu Thr Asn Asp Ile Asp Cys Thr Ala Arg Val
    50                  55                  60
Tyr Val Gln Pro Val His Gly Leu Thr Asn Tyr Ser Gly Thr Ala Phe
65                  70                  75                  80
Asp Ile Arg Gly Thr His Ile Thr Ile Asn Asp Phe Thr Ile Ala Pro
                85                  90                  95
Asp Gly Leu Thr Ala Tyr Leu Thr Asn Cys Asp Asn Gly Glu Lys Gln
            100                 105                 110
Val Trp His Phe Gln Tyr Val Asp Leu Asp Asp Pro Gln Gly Ala Asn
        115                 120                 125
Tyr Cys Ala Tyr Ser Cys Asn Gly Pro Glu Ile Val Glu Tyr Lys Cys
    130                 135                 140
Thr Thr Asn Thr Gly Tyr Ile Ser Pro Gln Gln Leu Gln Ala Val Lys
145                 150                 155                 160
Glu Ala Gln Ser Val Pro Asn Gly Asp Lys Ile His Leu Ala Gln Ala
                165                 170                 175
Asn Cys Pro Pro His Leu Tyr Cys Pro Leu Tyr Tyr
            180                 185
```

<210> SEQ ID NO 86
<211> LENGTH: 567
<212> TYPE: DNA
<213> ORGANISM: Parafontaria tonominea

<400> SEQUENCE: 86

```
atgacttcga tcattctcct cacgactgta gcactgatcg ttatgctggc cgaattgggc    60
tgggctgtgt caggtttgac ttgcgaccag ctccccaatg tcatcccacc tggcattagc   120
gctttcgctt ccaacaatcc ttttgaattc tcgtatgtgt tgactaacga tatcgactgt   180
```

| | |
|---|---:|
| accgcacgag tctatgtaca gcctgtacat ggactgacca attacagtgg aacagcattt | 240 |
| gacatcagag gaactcacat aacaataaat gacttcacca ttgctcccga tggtctgaca | 300 |
| gcctatttga ctaattgtga taatggagaa aaacaggttt ggcattttca atatgtcgac | 360 |
| ctagatgatc cccaaggtgc caactactgt gcatactctt gcaatggtcc cgaaatagtg | 420 |
| gaatacaaat gcactacgaa tactggatac atatcgcctc aacaactcca agctgtaaaa | 480 |
| gaggcacaat cagtcccaaa tggtgacaag atccatctag cccaggccaa ttgccctcct | 540 |
| cacctttact gtcctctcta ttactaa | 567 |

<210> SEQ ID NO 87
<211> LENGTH: 189
<212> TYPE: PRT
<213> ORGANISM: Parafontaria tonominea

<400> SEQUENCE: 87

```
Met Thr Ser Ile Ile Leu Leu Thr Thr Val Ala Leu Ile Val Met Leu
1               5                   10                  15

Ala Glu Leu Gly Trp Ala Gln Pro Ser Gly Leu Thr Cys Asp Gln Leu
            20                  25                  30

Pro Lys Val Ser Pro Gly Ile Ser Ala Phe Thr Phe Asn Asn Pro
        35                  40                  45

Phe Glu Phe Ser Tyr Val Leu Thr His Asp Ile Asp Cys Thr Ala Arg
    50                  55                  60

Val Tyr Val Gln Pro Val His Gly Leu Thr Asn Tyr Ser Gly Thr Ala
65                  70                  75                  80

Phe Asp Ile Arg Gly Thr His Ile Thr Ile Asn Asp Phe Thr Ile Ala
                85                  90                  95

Pro Asp Gly Leu Thr Ala Tyr Leu Thr Asn Cys Asp Asn Gly Glu Lys
            100                 105                 110

Gln Val Trp His Phe Gln Tyr Val Asp Leu Asp Asp Pro Gln Gly Ala
        115                 120                 125

Asn Tyr Cys Ala Tyr Ser Cys Asn Gly Ser Glu Ile Val Glu Tyr Lys
    130                 135                 140

Cys Thr Thr Asn Thr Gly Tyr Ile Ser Pro Gln Gln Leu Gln Ala Val
145                 150                 155                 160

Lys Glu Ala Gln Ser Val Pro Asn Gly Asp Lys Ile His Pro Ala Gln
                165                 170                 175

Ala Asn Cys Pro Pro His Leu Tyr Cys Pro Leu Tyr Tyr
            180                 185
```

<210> SEQ ID NO 88
<211> LENGTH: 570
<212> TYPE: DNA
<213> ORGANISM: Parafontaria tonominea

<400> SEQUENCE: 88

| | |
|---|---:|
| atgacttcga tcattctcct cacgactgta gcactgatcg ttatgttggc cgaattgggc | 60 |
| tgggctcaac cttcaggtct cacttgcgac cagctcccca agtcagtcc acctggcatt | 120 |
| agtgctttca ctttcaacaa tcctttgaa ttctcgtatg tgctgactca cgatatcgac | 180 |
| tgtaccgcac gagtctacgt acagcctgta catggactga ccaattacag tggaactgca | 240 |
| tttgacatca gaggaactca cataacaata aatgacttca ccattgctcc cgatggtctg | 300 |
| acagcctatt tgactaattg tgataatgga gaaaaacagg tttggcattt tcaatatgtc | 360 |
| gacctagatg atccccaagg tgccaactat tgtgcatact cttgcaatgg ttccgaaata | 420 |

```
gtggaataca aatgcactac gaatactgga tacatatcgc ctcaacaact ccaggctgta    480
aaagaggcac aatcagtccc aaatggtgac aagatccatc cagcccaggc caattgccct    540
cctcaccttt actgtcctct ctattactaa                                    570
```

```
<210> SEQ ID NO 89
<211> LENGTH: 190
<212> TYPE: PRT
<213> ORGANISM: Riukiaria semicircularis semicircularis

<400> SEQUENCE: 89
```

```
Met Thr Ser Ile Met Leu Cys Leu Thr Leu Ala Leu Thr Ala Met Met
1               5                   10                  15

Ala Glu Leu Gly Cys Ala Gln Pro Ala Glu Gly Pro Ser Cys Glu Asn
            20                  25                  30

Leu Pro Lys Val Val Pro Gly Ile Asp Ala Phe Val Ser His Asn
        35                  40                  45

Pro Phe Glu Phe Glu Phe Val Leu Ser Asn Ser Leu Asp Cys Thr Ala
    50                  55                  60

Arg Val Tyr Val Gln Pro Ala Arg Gly Tyr Thr Asn Tyr Ser Gly Thr
65                  70                  75                  80

Ala Phe Asp Ile Arg Lys Asn His Ile Asp Ile Asn Asp Phe Leu Ile
                85                  90                  95

Gly Ala Asp Gly Leu Thr Ala Tyr Leu Thr Asn Cys Asp Thr Gly Ala
            100                 105                 110

Lys Gln Val Trp His Phe Gln Tyr Thr Asp Leu Asp Asp Pro Leu Gly
        115                 120                 125

Ala Asn Tyr Cys Ala Tyr Ser Cys Asp Gly Ala Ser Ile Val Glu Tyr
    130                 135                 140

Lys Cys Thr Ser Asn Thr Gly Tyr Ile Ser Gln Lys Gln Lys Asp Ala
145                 150                 155                 160

Val Ala Glu Ala Lys Lys Val Pro Asn Gly Asp Lys Ile His Pro Gly
                165                 170                 175

Gln Val Asn Cys Pro Pro Asn Pro Phe Cys Pro Phe Tyr Ser
            180                 185                 190
```

```
<210> SEQ ID NO 90
<211> LENGTH: 573
<212> TYPE: DNA
<213> ORGANISM: Riukiaria semicircularis semicircularis

<400> SEQUENCE: 90
atgacttcga tcatgctctg tttaacttta gcactgactg ctatgatggc cgaattgggc     60
tgtgctcaac tgctgaaggc ccttcctgcg aaaatctccc caaagtcgt cccaccaggc    120 atcgatgctt tcgttcccca caatcctttt gaatttgagt ttgtgttgag caacagtttg    180
gactgcaccg cacgtgtcta cgtgcagcct gcacgtggat acaccaatta cagtggcacc    240
gcatttgata taagaaaaaa tcatattgac attaacgact ttctgatcgg tgctgatgga    300
ttgaccgcct atttaaccaa ttgtgatacc ggggcaaaac aagtttggca ttttcaatat    360
accgacctcg atgatcccct gggtgccaac tattgtgcat actcatgcga tggtgcctct    420
atagtggaat acaatgcac ttccaatact ggctacatat cgcaaaagca aaggatgca    480 gtggcagagg ctaaaaaagt cccaaatggt gacaagatcc acccaggcca ggtcaattgc    540
cctcctaacc ctttctgccc cttctatagc taa                                573
```

<210> SEQ ID NO 91
<211> LENGTH: 26
<212> TYPE: DNA
<213> ORGANISM: Artificial sequence
<220> FEATURE:
<223> OTHER INFORMATION: Primer

<400> SEQUENCE: 91
ggacagcctt ttcgactaat tgtgat                                      26

<210> SEQ ID NO 92
<211> LENGTH: 25
<212> TYPE: DNA
<213> ORGANISM: Artificial sequence
<220> FEATURE:
<223> OTHER INFORMATION: Primer

<400> SEQUENCE: 92
cccaaggtgc caactactgt gcata                                       25

<210> SEQ ID NO 93
<211> LENGTH: 27
<212> TYPE: DNA
<213> ORGANISM: Artificial sequence
<220> FEATURE:
<223> OTHER INFORMATION: Primer

<400> SEQUENCE: 93
gcctggagtt gttgaggcga tatgtat                                     27

<210> SEQ ID NO 94
<211> LENGTH: 27
<212> TYPE: DNA
<213> ORGANISM: Artificial sequence
<220> FEATURE:
<223> OTHER INFORMATION: Primer

<400> SEQUENCE: 94
gcaagagtag cctatgcaca gtagttg                                     27

<210> SEQ ID NO 95
<211> LENGTH: 27
<212> TYPE: DNA
<213> ORGANISM: Artificial sequence
<220> FEATURE:
<223> OTHER INFORMATION: Primer

<400> SEQUENCE: 95
ccgatggtct gacagcctat ttgacta                                     27

<210> SEQ ID NO 96
<211> LENGTH: 26
<212> TYPE: DNA
<213> ORGANISM: Artificial sequence
<220> FEATURE:
<223> OTHER INFORMATION: Primer

<400> SEQUENCE: 96
ccccaaggtg ccaactactg tgcata                                      26

<210> SEQ ID NO 97
<211> LENGTH: 29
<212> TYPE: DNA
<213> ORGANISM: Artificial sequence
<220> FEATURE:
<223> OTHER INFORMATION: Primer

<400> SEQUENCE: 97
ggcgatatgt atccagtatt cgtagtgca                                29

<210> SEQ ID NO 98
<211> LENGTH: 27
<212> TYPE: DNA
<213> ORGANISM: Artificial sequence
<220> FEATURE:
<223> OTHER INFORMATION: Primer

<400> SEQUENCE: 98
cgggaccatt gcaagagtat gcacagt                                  27

<210> SEQ ID NO 99
<211> LENGTH: 27
<212> TYPE: DNA
<213> ORGANISM: Artificial sequence
<220> FEATURE:
<223> OTHER INFORMATION: Primer

<400> SEQUENCE: 99
ctgacagcct atttgactaa ttgtgat                                  27

<210> SEQ ID NO 100
<211> LENGTH: 25
<212> TYPE: DNA
<213> ORGANISM: Artificial sequence
<220> FEATURE:
<223> OTHER INFORMATION: Primer

<400> SEQUENCE: 100
gcatactctt gcaatggttc cgaaa                                    25

<210> SEQ ID NO 101
<211> LENGTH: 27
<212> TYPE: DNA
<213> ORGANISM: Artificial sequence
<220> FEATURE:
<223> OTHER INFORMATION: Primer

<400> SEQUENCE: 101
gcctggagtt gttgaggcga tatgtat                                  27

<210> SEQ ID NO 102
<211> LENGTH: 25
<212> TYPE: DNA
<213> ORGANISM: Artificial sequence
<220> FEATURE:
<223> OTHER INFORMATION: Primer

<400> SEQUENCE: 102
cggaaccatt gcaagagtat gcaca                                    25

<210> SEQ ID NO 103
<211> LENGTH: 26
<212> TYPE: DNA
<213> ORGANISM: Artificial sequence
<220> FEATURE:
<223> OTHER INFORMATION: Primer

<400> SEQUENCE: 103
gacttcctca tcgctcctga ttgtat                                   26

```
<210> SEQ ID NO 104
<211> LENGTH: 24
<212> TYPE: DNA
<213> ORGANISM: Artificial sequence
<220> FEATURE:
<223> OTHER INFORMATION: Primer

<400> SEQUENCE: 104
cgtcgaggat cccaagggtg ccaa                                          24

<210> SEQ ID NO 105
<211> LENGTH: 24
<212> TYPE: DNA
<213> ORGANISM: Artificial sequence
<220> FEATURE:
<223> OTHER INFORMATION: Primer

<400> SEQUENCE: 105
gccagctata ttggaagtgc attt                                          24

<210> SEQ ID NO 106
<211> LENGTH: 26
<212> TYPE: DNA
<213> ORGANISM: Artificial sequence
<220> FEATURE:
<223> OTHER INFORMATION: Primer

<400> SEQUENCE: 106
ccatcgcaag agtatgcgca atagtt                                        26

<210> SEQ ID NO 107
<211> LENGTH: 24
<212> TYPE: DNA
<213> ORGANISM: Artificial sequence
<220> FEATURE:
<223> OTHER INFORMATION: Primer

<400> SEQUENCE: 107
atgacttcga tcattctcct cacg                                          24

<210> SEQ ID NO 108
<211> LENGTH: 25
<212> TYPE: DNA
<213> ORGANISM: Artificial sequence
<220> FEATURE:
<223> OTHER INFORMATION: Primer

<400> SEQUENCE: 108
ttagtaatag agggacaga aaagg                                          25

<210> SEQ ID NO 109
<211> LENGTH: 24
<212> TYPE: DNA
<213> ORGANISM: Artificial sequence
<220> FEATURE:
<223> OTHER INFORMATION: Primer

<400> SEQUENCE: 109
atgacttcga tcattctcct cacg                                          24

<210> SEQ ID NO 110
<211> LENGTH: 27
<212> TYPE: DNA
<213> ORGANISM: Artificial sequence
<220> FEATURE:
<223> OTHER INFORMATION: Primer
```

<400> SEQUENCE: 110
ttagtaatag agaggacagt aaaggtg                                    27

<210> SEQ ID NO 111
<211> LENGTH: 24
<212> TYPE: DNA
<213> ORGANISM: Artificial sequence
<220> FEATURE:
<223> OTHER INFORMATION: Primer

<400> SEQUENCE: 111
atgacttcga tcattctcct cacg                                       24

<210> SEQ ID NO 112
<211> LENGTH: 25
<212> TYPE: DNA
<213> ORGANISM: Artificial sequence
<220> FEATURE:
<223> OTHER INFORMATION: Primer

<400> SEQUENCE: 112
ttagtaatag agaggacagt aaagg                                      25

<210> SEQ ID NO 113
<211> LENGTH: 26
<212> TYPE: DNA
<213> ORGANISM: Artificial sequence
<220> FEATURE:
<223> OTHER INFORMATION: Primer

<400> SEQUENCE: 113
atgacttcga tcatgctctg tttaac                                     26

<210> SEQ ID NO 114
<211> LENGTH: 25
<212> TYPE: DNA
<213> ORGANISM: Artificial sequence
<220> FEATURE:
<223> OTHER INFORMATION: Primer

<400> SEQUENCE: 114
ttagctatag aaggggcaga aaggg                                      25

<210> SEQ ID NO 115
<211> LENGTH: 40
<212> TYPE: DNA
<213> ORGANISM: Artificial sequence
<220> FEATURE:
<223> OTHER INFORMATION: Primer

<400> SEQUENCE: 115
catcgggcgc ggatccatga cttcgatcat tctcctcacg                      40

<210> SEQ ID NO 116
<211> LENGTH: 41
<212> TYPE: DNA
<213> ORGANISM: Artificial sequence
<220> FEATURE:
<223> OTHER INFORMATION: Primer

<400> SEQUENCE: 116
acttctcgac aagcttttag taatagaggg gacagaaaag g                    41

```
<210> SEQ ID NO 117
<211> LENGTH: 40
<212> TYPE: DNA
<213> ORGANISM: Artificial sequence
<220> FEATURE:
<223> OTHER INFORMATION: Primer

<400> SEQUENCE: 117
catcgggcgc ggatccatga cttcgatcat tctcctcacg                           40

<210> SEQ ID NO 118
<211> LENGTH: 43
<212> TYPE: DNA
<213> ORGANISM: Artificial sequence
<220> FEATURE:
<223> OTHER INFORMATION: Primer

<400> SEQUENCE: 118
acttctcgac aagcttttag taatagagag gacagtaaag gtg                      43

<210> SEQ ID NO 119
<211> LENGTH: 40
<212> TYPE: DNA
<213> ORGANISM: Artificial sequence
<220> FEATURE:
<223> OTHER INFORMATION: Primer

<400> SEQUENCE: 119
catcgggcgc ggatccatga cttcgatcat tctcctcacg                           40

<210> SEQ ID NO 120
<211> LENGTH: 41
<212> TYPE: DNA
<213> ORGANISM: Artificial sequence
<220> FEATURE:
<223> OTHER INFORMATION: Primer

<400> SEQUENCE: 120
acttctcgac aagcttttag taatagagag gacagtaaag g                        41

<210> SEQ ID NO 121
<211> LENGTH: 40
<212> TYPE: DNA
<213> ORGANISM: Artificial sequence
<220> FEATURE:
<223> OTHER INFORMATION: Primer

<400> SEQUENCE: 121
catcgggcgc ggatccatga cttcgatcat gctctgttta                           40

<210> SEQ ID NO 122
<211> LENGTH: 41
<212> TYPE: DNA
<213> ORGANISM: Artificial sequence
<220> FEATURE:
<223> OTHER INFORMATION: Primer

<400> SEQUENCE: 122
acttctcgac aagcttttag ctatagaagg ggcagaaagg g                        41
```